United States Patent
Iacono et al.

(10) Patent No.: US 12,178,843 B2
(45) Date of Patent: *Dec. 31, 2024

(54) CYCLOSPORINE FORMULATIONS FOR USE IN THE TREATMENT OF BRONCHIOLITIS OBLITERANS SYNDROME (BOS)

(71) Applicant: Breath Therapeutics GmbH, Munich (DE)

(72) Inventors: Aldo Iacono, Cockeysville, MD (US); Oliver Denk, Muensing (DE); Gerhard Boerner, Utting (DE)

(73) Assignee: Breath Therapeutics GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/321,788

(22) Filed: May 23, 2023

(65) Prior Publication Data

US 2023/0364182 A1 Nov. 16, 2023

Related U.S. Application Data

(63) Continuation of application No. 17/935,140, filed on Sep. 26, 2022, now Pat. No. 11,701,403, which is a continuation of application No. 17/046,307, filed as application No. PCT/EP2019/058958 on Apr. 9, 2019, now Pat. No. 11,484,566.

(60) Provisional application No. 62/656,226, filed on Apr. 11, 2018.

(30) Foreign Application Priority Data

May 14, 2018 (EP) .................................. 18172067

(51) Int. Cl.
A61K 38/13 (2006.01)
A61K 9/00 (2006.01)
A61P 11/00 (2006.01)
A61K 45/06 (2006.01)

(52) U.S. Cl.
CPC ............ *A61K 38/13* (2013.01); *A61K 9/0078* (2013.01); *A61P 11/00* (2018.01); *A61K 45/06* (2013.01)

(58) Field of Classification Search
CPC ...... A61K 38/13; A61K 9/0078; A61K 45/06; A61K 47/02; A61K 47/183; A61K 47/24; A61K 9/127; A61K 9/19; A61K 47/26; A61P 11/00
See application file for complete search history.

(56) References Cited

U.S. PATENT DOCUMENTS 11,484,566 B2 * 11/2022 Iacono ..................... A61K 9/19
11,701,403 B2 * 7/2023 Iacono ................... A61K 47/02
514/20.5

OTHER PUBLICATIONS

Behr et al (Journal of Aerosol Medicine and Pulmonary Drug Delivery, vol. 22, No. 2, 2009) (Year: 2009).*

* cited by examiner

*Primary Examiner* — Sudhakar Katakam
(74) *Attorney, Agent, or Firm* — Synergy IP Group AG; Lily Ackerman

(57) ABSTRACT

The present invention relates to a composition comprising cyclosporine A (CsA) for use in the prevention of bronchiolitis obliterans syndrome (BOS) in a double lung transplanted patient, or for the treatment of BOS or for the prevention or delay of the progression of BOS in a double lung transplanted patient being diagnosed with BOS, wherein the composition is administered to said patient by inhalation of said composition in aerosolized form comprising a therapeutically effective dose of cyclo-sporine A.

27 Claims, 6 Drawing Sheets

Kaplan-Meier Plot: Event-Free Survival Probability
(Event = BOS progression, re-transplant, or death)

Double Transplants Kaplan-Meier Plot:

Event-Free Survival (Event = BOS progression, re-transplant, or death)

Single Transplants Kaplan-Meier Plot: Event-Free Survival (Event = BOS progression, re-transplant, or death)

Kaplan-Meier Plot: Survival after Randomization (L-CsA vs. SOC)

Product-Limit Survival Estimates

Overall FEV1 trends by treatment group, adjusting for pre-randomization FEV$_1$ trends

Overall FEV$_1$ trends by treatment group, adjusting for pre-randomization FEV$_1$ trends

* For one SOC patient, an FEV₁ of 0 was imputed at the time the patient went on mechanical ventilation; this patient had no post-randomization PFT measurements

CYCLOSPORINE FORMULATIONS FOR USE IN THE TREATMENT OF BRONCHIOLITIS OBLITERANS SYNDROME (BOS)

CROSS REFERENCE TO RELATED APPLICATIONS

This application is a continuation of U.S. application Ser. No. 17/935,140, filed on Sep. 26, 2022, now U.S. Pat. No. 11,701,403 B2, which is a continuation of U.S. application Ser. No. 17/046,307, filed on Oct. 9, 2020, now U.S. Pat. No. 11,484,566 B2, which is a U.S. National Stage Application filed under 35 U.S.C. § 371 claiming the benefit of PCT Application No. PCT/EP2019/058958, filed on Apr. 9, 2019, which claims priority to and the benefit of European Application No. 18172067.3, filed on May 14, 2018, and U.S. Provisional Application Ser. No. 62/656,226, filed on Apr. 11, 2018, all of which are hereby incorporated herein by reference in their entireties.

FIELD OF THE INVENTION

The invention relates to pharmaceutical compositions comprising cyclosporine A (CsA) for use in the prevention of bronchiolitis obliterans syndrome (BOS) in a double lung transplanted patient or for the treatment of BOS or prevention or delay of the progression of BOS in a double lung transplanted patient being diagnosed with BOS.

BACKGROUND OF THE INVENTION

Lung transplantation has become an effective treatment option for a variety of chronic and end-stage lung diseases. Lung preservation techniques have been developed over time resulting in satisfactory short-term results (Hachem R R, Trulock E P. Bronchiolitis obliterans syndrome: pathogenesis and management. *Semin Thorac Cardiovasc Surg* 2004; 16:350-355). Immunosuppression is a key post-transplant intervention usually consisting of a triple therapy regimen, including systemic cyclosporine A (CsA) or tacrolimus, azathioprine or mycophenolate mofetil and corticosteroids (Knoop C, et al. Immunosuppressive therapy after human lung transplantation. *Eur Respir J* 2004; 23:159-171).

Both, the transplantation of a single lung lobe as well as the transplantation of both lung lobes is possible. Double lung transplantation is indicated in cases of cystic fibrosis, primary pulmonary hypertension, alpha-1-antitrypsin deficiency, emphysema with global insufficiency, frequent serious infections as well as idiopathic pulmonary fibrosis with complication by repeated infections.

Despite systemic immunosuppressive therapy with cyclosporine or tacrolimus, azathioprine or mycophenolate mofetil and corticosteroids, chronic rejection after lung transplantation is a severe pulmonary complication accounting for 30% of deaths in lung transplantation, thus making the evaluation for new therapeutic options desirable.

Development of bronchiolitis obliterans syndrome (BOS), a major contributor to pulmonary chronic graft dysfunction, is the leading cause of morbidity and mortality in long-term survivors of lung transplantation and remains the major limitation to long-term survival after lung transplantation. It occurs in 60 to 70% of transplant recipients who survive five years. The median time to development of BOS is approximately 18 months. Although the pathogenesis of BOS is multifactorial and is not completely understood, chronic rejection resulting from immune-dependent responses (acute rejection episodes) is considered to be the predominant cause of BOS (Moffatt-Bruce S., "Invited commentary", Ann Thorac Surg. 2009 September; 88 (3): 964-5. doi: 10.1016/j.athoracsur. 2009.06.014) after lung transplantation despite the use of systemic calcineurin inhibitors for immunosuppression (Iacono A T, et al. A randomized trial of inhaled cyclosporine in lung-transplant recipients. *N Engl J Med* 2006; 354:141-150). Once chronic rejection develops, airway damage is progressive and irreversible and patients eventually die of graft failure or pneumonia.

Currently, satisfactory therapeutic options for the effective treatment of BOS following double lung transplantation are not available. Augmented immunosuppression using higher doses of commonly used drugs for basic immunosuppression have been proven ineffective and are contemporarily associated with a higher adverse event rate over time due to the increased drug burden. Immunosuppressive antibodies may be useful for the prevention of acute pulmonary graft rejection but therapeutic attempts to treat chronic rejection have produced disappointing results. From the pathomechanistic point of view this is comprehensive because acute lung graft rejection is basically a vasculitis starting with deleterious reactions on the epithelium of blood vessels. In contrast, although still not completely understood in all details, there is consent that the origin of chronic lung rejection resides in the lung lumen, i.e. the bronchioli, and therefore is rather a bronchiolitis than a vasculitis. Systemically administered drugs thus are challenged to cross the capillary-alveolar barrier. Photopheresis is frequently selected as a last resort measure in high-stage BOS patients and performed rather for psychological purposes than for medical reasons. Thus, new therapies for the prevention and treatment of pulmonary chronic graft rejection, especially after double lung transplantation, are highly desired.

Currently, the median survival is 4.6 years in single lung transplanted patients, whereas it is 6.6 years in double lung transplanted patients. It has been shown that this different survival is related to a considerable delay in the onset of BOS after double lung transplantation compared to single lung transplantation (Hadjiliadis D, et al. Is transplant Operation important in determining posttransplant risk of bronchiolitis obliterans syndrome in lung transplant recipients? *Chest* 2002; 122:1168-1175).

Successful prevention of BOS or, in case in which BOS has been diagnosed already, a delay of the progression of BOS is identified as a major requirement to improve the outcome of lung transplantation.

It has been suggested that the most important cause of BOS is T-lymphocyte activation by major histocompatibility antigen- or immune-dependent mechanisms (Soubani A O, Uberti J P. Bronchiolitis obliterans following haematopoietic stem cell transplantation. *Eur Respir J* 2007; 29:1007-1019; Halloran P F, et al. The "injury response": A concept linking nonspecific injury, acute rejection, and long-term outcomes. *Transplant Proc* 1997; 29:79-81). From systemic application, it is well known that CsA blocks T-lymphocyte proliferation by inhibiting the phosphatase activity of calcineurin enzyme and reduces the expression of several cytokines genes (e.g. for interleukin [IL]-2) that are normally induced in T-cell activation.

While most solid organ transplants are inaccessible to localized immunotherapy, lung transplants are the exception due to their unique communication with the external environment making inhalation a therapeutic option.

It has been proposed that a topical application of CsA to the lungs may improve efficacy with the potential to reduce systemic exposure of toxic immunosuppressants (Iacono A, et al. Dose related reversal of acute lung rejection by aerosolized ciclosporin. *Am J Respir Crit Care Med* 1997; 155:1690-1698). Cyclosporine A is a cyclic polypeptide consisting of 11 amino acids. It is produced as a metabolite by the fungus species *Beauveria nivea*. Cyclosporine is an immunosuppressant belonging to the group of calcineurin inhibitors which has been used to prevent graft rejection after organ transplantation in most of the post-transplant regimens since the early 1980s in Europe.

The use of aerosolized cyclosporine for the prevention and treatment of pulmonary diseases has been described in WO 00/45834 A2. More specifically, delivery of cyclosporine to the transplanted lung by aerosol inhalation is disclosed. The cyclosporine may be administered in in either dry powder or wet form, such as cyclosporine powder aerosolized in propylene glycol. The document, however, is silent on the use of cyclosporine in the form of liposomal cyclosporine A. Furthermore, none of the treated subjects is reported to have developed bronchiolitis obliterans.

From the study of Corcoran et al. (Preservation of post-transplant lung function with aerosol cyclosporin. *Eur Respir J* 2004; 23:378-383) it has been concluded that a CsA propylene glycol (CsA-PG) peripheral lung deposition of approximately 5 mg or higher would improve lung function of transplant patients whereas lower doses resulted in a decline. From the latter study, it was derived that an effective threshold of ≥15 mg/week or ≥2 mg/day CsA deposited in the periphery of the lung(s) should be achieved for a therapeutic effect.

A. T. Iacono et al. report in Eur. Resspir. J. 2004; 23:384-390 on the aerosol cyclosporine therapy in lung transplant recipients with bronchiolitis obliterans. In this study also, cyclosporine was used in powder form dissolved in propylene glycol. Most notably, double lung transplant recipients were reported to be at increased risk of death after the onset of bronchiolitis obliterans compared to single lung transplant recipients.

A phase II clinical trial with 58 lung transplanted patients showed after up to two years treatment with inhaled CsA-PG a statistically significant difference in BOS-free survival and overall survival in favour of CsA-PG therapy versus placebo (lacono A T, et al. A randomized trial of inhaled cyclosporine in lung-transplant recipients. *N Engl J Med* 2006; 354:141-150). In contrast, a multi-centre phase III clinical trial showed no efficacy beyond that of standard of care when CsA was used as supplemental targeted therapy to prevent chronic rejection in lung transplant patients. The outcome of this study is at odds with numerous preclinical and clinical studies which allow for expectation of a therapeutic response. From this result, it was concluded that administering a cyclosporine aerosol to this highly vulnerable patient population is not without challenges and that one or more of these challenges may have influenced the study outcome. It was concluded from an analysis of these challenges that the use of a more convenient delivery system administering drug at more frequent intervals within a setting of inhalation treatment or systemic replacement may prove successful (Niven R W, et al. The challenges of developing an inhaled cyclosporine product for lung transplant patients. *Respiratory Drug Delivery* 2012; 51-60).

With respect to the CsA-PG formulation, patient intolerance and lack of adherence due to the long inhalation time of up to 30 min have been reported (Corcoran T E. Inhaled delivery of aerosolized cyclosporine. *Adv Drug Deliv Rev* 2006; 58:1119-1127). Propylene glycol is known to be hyperosmotic with potential to be intolerable by the patients thus requiring pre-medication with a bronchodilator and local anaesthetic drug.

In view of these issues, a new liposomal formulation of cyclosporine for inhalation use was developed. The formulation is described in WO 2007/065588.

Furthermore, new inhalation systems have been proposed for the inhalation of CsA, which are supposed to allow a more efficient deposition of CsA in the lungs. Examples of such systems are vibrating membrane nebulizers. Such inhalation systems achieve a better targeting of the drug by production of particles with the appropriate size for high peripheral deposition. Also, the high drug delivery rate of such devices supports much shorter inhalation times which are expected to be advantageous with respect to patient adherence.

In a Phase Ib clinical trial the lung deposition and pharmacokinetics of 10 and 20 mg radio-labelled aerosolized liposomal CsA (L-CsA) were investigated in five double lung transplanted patients and seven single lung transplanted patients. The aerosol was generated with an eFlow® nebulizer. Patients were given a single dose application of 10 or 20 mg of liposomal CsA, which was well tolerated. It was shown that 40±6% (for the 10 mg dose) and 33±7% (for the 20 mg dose), respectively, was deposited in the lung. This resulted in a peripheral lung dose of 2.2±0.5 mg (for the 10 mg dose) and 3.5±0.9 mg (for the 20 mg dose), respectively. Assuming single or twice daily dosing with 10 mg nominal drug amount of L-CsA, 14 and 28 mg/week peripheral deposition could be achieved, respectively. Overall inhalation time for the 10 and 20 mg nominal dose was approximately 9±1 min and 20±5 min, respectively. In single lung transplanted patients, almost the entire deposition (88-90%) occurred in the transplanted part of the lung. There were no statistically significant differences between patients with single and double lung transplantation. Although several preclinical and clinical studies have been performed with inhaled CsA, the conclusions with respect to the actual efficacy of inhaled cyclosporine for double lung transplanted patients are contradicting. Thus, presently available studies do not allow any conclusion with respect to the actual efficacy of inhaled cyclosporine in the treatment of pulmonary chronic graft rejection and, more specifically bronchiolitis obliterans syndrome (BOS) after lung transplantation.

Bronchiolitis obliterans syndrome (BOS), has been defined physiologically as a sustained 20% or greater decline of $FEV_1$ from maximum post-transplant values. Existing immunosuppressive regimens remain largely ineffective. Increased cyclosporine may be deposited in the lung by inhalation resulting in higher airway concentrations which may lead to better efficacy for the treatment of BOS.

WO 2016/146645 A1 discloses a cyclosporine liquid formulation for use as an aerosol for inhalation in a method of preventing or treating pulmonary chronic graft rejection in single lung transplanted patients. In specific embodiments, the pulmonary chronic graft rejection is characterized by bronchiolitis obliterans syndrome (BOS). The document, however, while emphasizing the unexpectedly successful treatment of the subpopulation of single lung transplanted patients, does not allow to draw any conclusion for the treatment of double lung transplanted patients, especially not for those double lung transplanted patients who have already developed bronchiolitis obliterans syndrome (BOS). In view of this disclosure, a successful treatment of double lung transplanted patients who already have developed BOS cannot be expected.

A. Iacono et al. report in The Journal of Heart and Lung Transplantation, Vol 37, No 4S, 211 on the stabilization of lung function and survival improvement by aerosolized liposomal cyclosporine A (L-CsA) for Bronchiolitis Obliterans Syndrome. The document, however, is silent on the outcome of the study and therefore on the effectiveness of the treatment with regard to specific patient subpopulations, namely either single lung transplant recipients or double lung transplant recipients.

Accordingly, there is still need for the prevention or an effective treatment of the bronchiolitis obliterans syndrome (BOS) when developed and diagnosed in patients who have received double lung transplantation. Therefore, it is an object of the present invention to provide means for the successful prevention or treatment especially of double lung transplanted patients who already have developed and have been diagnosed with BOS, especially with more severe forms of BOS, such as BOS 1 or BOS 2. Further objects of the present invention will become apparent in view of the present disclosure.

SUMMARY OF THE INVENTION

In a first aspect, the present invention relates to a composition comprising liposomal cyclosporine A (L-CsA) for use in the prevention of bronchiolitis obliterans syndrome (BOS) in a double lung transplanted patient, or for the treatment of BOS or the prevention or delay of the progression of BOS in a double lung transplanted patient being diagnosed with BOS, wherein the composition is administered to said patient by inhalation of said composition in aerosolized form comprising a therapeutically effective dose of cyclosporine A.

In a second aspect, the present invention relates to a method for preventing bronchiolitis obliterans syndrome (BOS) in a double lung transplanted patient or for treating BOS or for preventing or delaying the progression of BOS in a double lung transplanted patient being diagnosed with BOS, the method comprising the steps of
  (a) identifying a patient who has received a double lung transplant and is at risk to develop or subsequently has developed BOS, specifically BOS grade 1 or higher; and
  (b) administering to said patient a therapeutically effective dose of aerosolised liposomal cyclosporin A (L-CsA) by inhalation.

DETAILED DESCRIPTION OF THE INVENTION

Figure 1:
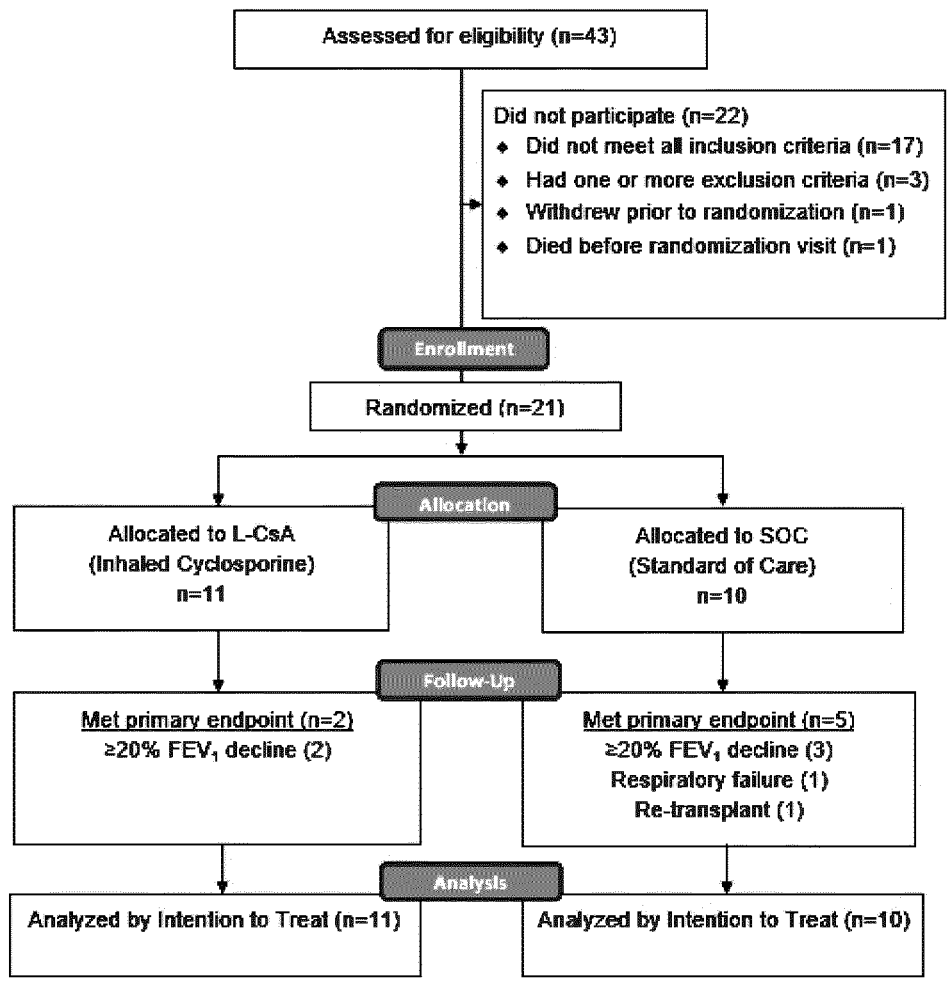
FIG. 1 shows a flow chart summarizing the details of the enrollment of single and double lung transplanted patients in the clinical study as further described below.

The following terms or expressions as used herein should normally be interpreted as outlined in this section, unless defined otherwise by the description or unless the specific context indicates or requires otherwise:

The terms "consist of", "consists of" and "consisting of" as used herein are so-called closed language meaning that only the mentioned components are present. The terms "comprise", "comprises" and "comprising" as used herein are so-called open language, meaning that one or more further components may or may not also be present.

The term "active pharmaceutical ingredient" (also referred to as "API" throughout this document) refers to any type of pharmaceutically active compound or derivative that is useful in the prevention, diagnosis, stabilization, treatment, or—generally speaking—management of a condition, disorder or disease.

The term "therapeutically effective amount" as used herein refers to a dose, concentration or strength which is useful for producing a desired pharmacological effect. In the context of the present invention, the term "therapeutically effective" also includes prophylactic activity. The therapeutic dose is to be defined depending on the individual case of application. Depending on the nature and severity of the disease, route of application as well as height and state of the patient, a therapeutic dose is to be determined in a way known to the skilled person.

In the context of the present invention, a "pharmaceutical composition" is a preparation of at least one API and at least one adjuvant, which, in the simplest case, can be, for example, an aqueous liquid carrier such as water or saline.

The expressions 'a' or 'an' does not exclude a plurality; i.e. the singular forms 'a', 'an' and 'the' should be understood as to include plural referents unless the context clearly indicates or requires otherwise. In other words, all references to singular characteristics or limitations of the present disclosure shall include the corresponding plural characteristic or limitation, and vice versa, unless explicitly specified otherwise or clearly implied to the contrary by the context in which the reference is made.

The terms 'a', 'an' and 'the' hence have the same meaning as 'at least one' or as 'one or more' unless defined otherwise. For example, reference to 'an ingredient' includes mixtures of ingredients, and the like.

The expressions, 'one embodiment', 'an embodiment', 'a specific embodiment' and the like mean that a particular feature, property or characteristic, or a particular group or combination of features, properties or characteristics, as referred to in combination with the respective expression, is present in at least one of the embodiments of the invention. The occurrence of these expressions in various places throughout this description do not necessarily refer to the same embodiment. Moreover, the particular features, properties or characteristics may be combined in any suitable manner in one or more embodiments.

The term 'treatment', as used herein, includes a therapeutic intervention capable of effecting a cure of a disease, condition or symptom; but also an improvement, amelioration, control, control of progression, and the like.

The term 'prevention' is meant to include the prevention or delay of progression of a disease, condition or symptom, or the prevention of further growth and spread and of a reoccurrence or progression after an initial improvement or after initial removal of the cause of the disease, condition or symptom.

The terms 'patient' and 'subject' are used synonymously herein. Typically, the terms refer to humans. However, the invention is not limited to humans only and may be employed in animals if required.

The terms 'essentially', 'about', 'approximately', 'substantially" and the like in connection with an attribute or value include the exact attribute or the precise value, as well as any attribute or value typically considered to fall within a normal range or variability accepted in the technical field concerned. For example, 'substantially free of water" means that no water is deliberately included in a formulation, but does not exclude the presence of residual moisture.

When used herein the term 'about' or 'ca.' will compensate for variability allowed for in the pharmaceutical industry and inherent in pharmaceutical products, such as differences in content due to manufacturing variation and/or time-induced product degradation. The term allows for any variation, which in the practice of pharmaceuticals would allow the product being evaluated to be considered bioequivalent in a mammal to the recited strength of a claimed product.

A 'vehicle', as used herein, may generically mean any compound, construct or material being part of a formulation which aids, enables, or improves the delivery of the biologically active compound or material.

The term 'pharmaceutically acceptable' means that the compound or mixture is useful in preparing a pharmaceutical composition that is generally safe, non-toxic and neither biologically nor otherwise undesirable and includes that which is acceptable for human pharmaceutical use.

In the broadest sense, the present invention relates to a composition comprising cyclosporine A (CsA) for use in the prevention of bronchiolitis obliterans syndrome (BOS) in a double lung transplanted patient, or for the treatment of BOS or for the prevention or delay of the progression of BOS in a double lung transplanted patient being diagnosed with BOS, wherein the composition is administered to said patient by inhalation of said composition in aerosolized form comprising a therapeutically effective dose of cyclosporine A.

Furthermore, the present invention relates to a composition comprising cyclosporine A (CsA) for use in the treatment of bronchiolitis obliterans syndrome (BOS) or for the prevention or delay of the progression of BOS in a double lung transplanted patient being diagnosed with BOS, wherein the composition is administered to said patient by inhalation of said composition in aerosolized form comprising a therapeutically effective dose of cyclosporine A.

In a first aspect, more specifically, the present invention relates to a composition comprising liposomal cyclosporine A (L-CsA) for use in the prevention of bronchiolitis obliterans syndrome (BOS) in a double lung transplanted patient, or for the treatment of BOS or for the prevention or delay of the progression of BOS in a double lung transplanted patient being diagnosed with BOS, wherein the composition is administered to said patient by inhalation of said composition in aerosolized form comprising a therapeutically effective dose of cyclosporine A (CsA).

The compositions for use according to the present invention comprise cyclosporine A (CsA) or, more specifically liposomal CsA (L-CsA) in a therapeutically effective dose or amount as described further below and as described, for example, in detail in aforementioned WO 2007/065588. The pharmaceutical compositions for use according to the present invention, in specific embodiments, may be liquid compositions. In these embodiments, the compositions for use according to the present invention comprise L-CsA and a liquid carrier or vehicle in which the L-CsA can be dissolved, dispersed or suspended. In specific embodiments, these compositions comprise a therapeutically effective dose of CsA, an aqueous carrier liquid, a first solubility enhancing substance selected from the group of phospholipids and a second solubility enhancing substance selected from the group of non-ionic surfactants to form the liposomally solubilized CsA (L-CsA).

Phospholipids that may be comprised by the compositions for use according to the present invention are, in particular, mixtures of natural or enriched phospholipids, for example, lecithines such as the commercially available Phospholipon G90, 100, or Lipoid 90, S 100. Accordingly, in preferred embodiments, the phospholipids that may be comprised by the compositions for use according to the present invention may be selected from the group of phospholipids is a mixture of natural phospholipids.

Phospholipids are amphiphilic lipids which contain phosphorus. Known also as phosphatides, they play an important role in nature, especially as the double layer forming constituents of biological membranes and frequently used for pharmaceutical purposes are those phospholipids which are chemically derived from phosphatidic acid. The latter is a (usually doubly) acylated glycerol-3-phosphate in which the fatty acid residues may be of different lengths. The derivatives of phosphatidic acids are, for example, the phosphocholines or phosphatidylcholines, in which the phosphate group is additionally esterified with choline, as well as phosphatidylethanolamine, phosphatidylinositols etc. Lecithins are natural mixtures of various phospholipids which usually contain a high proportion of phosphatidylcholines. Preferred phospholipids according to the invention are lecithins as well as pure or enriched phosphatidylcholines such as dimyristoylphospatidylcholine, di-palmitoylphosphatidylcholine and distearoylphosphatidylcholine.

In specific embodiments, the first solubility enhancing substance selected from the group of phospholipids comprised by the compositions for use according to the present invention may be selected from the group of phospholipids and may be a lecithine, more specifically, a lecithin containing unsaturated fatty acid residues. In yet further preferred embodiments, the membrane-forming substance selected from the group of phospholipids is a lecithin selected from the group consisting of soy bean lecitin, Lipoid S100, Phospholipon® G90, 10, preferably Lipoid S100, or a comparable lecithin. In further preferred embodiments, the membrane-forming substance selected from the group of phospholipids is selected from Lipoid S100, Lipoid S75, particularly Lipoid S100.

In specific embodiments, the weight ratio of the first membrane forming substance selected from the group of phospholipids as described above to CsA is selected in the range of from about 8:1 to about 11:1, preferably from about 8.5:1 to about 10:1, for example, about 13:1.

The pharmaceutical compositions for use according to the present invention may further comprise a second solubility-enhancing substance or two or more different solubility-enhancing substances selected from the group of non-ionic surfactants. Non-ionic surfactants have—as other surfactants—at least one rather hydrophilic and at least one rather lipophilic molecular region. There are monomeric, low molecular weight non-ionic surfactants and non-ionic surfactants having an oligomeric or polymeric structure. Examples of suitable non-ionic surfactants that may be comprised by the present invention comprise polyoxyethylene alkyl ethers, polyoxyethylene sorbitan fatty acid esters such as, for example, polyoxyethylene sorbitan oleate, sorbitan fatty acid esters, poloxamers, vitamin E-TPGS (D-α-tocopheryl-polyethyleneglycol-1000-succinate) and tyloxapol.

In specific embodiments, the second solubility-enhancing substance selected from the group of non-ionic surfactants may be selected from the group of polysorbates and vitamin E-TPGS, preferably is selected from the group of polysorbates. In a particularly preferred embodiment, the solubility-enhancing substance selected from the group of non-ionic surfactants is polysorbate 80.

In specific embodiments of the present pharmaceutical compositions, the amount of the first membrane-forming substance selected from the group of phospholipids, preferably the lecithin, is larger than the amount of the second solubility-enhancing substance selected from the group of non-ionic surfactants. In exemplary embodiments, the weight ratio of the first membrane forming substance selected from the group of phospholipids, preferably the lecithin, to the second solubility enhancing substance selected from the group of non-ionic surfactants, preferably the polysorbate, is selected in the range of from about 15:1 to about 9:1, preferably from about 14:1 to about 12:1, for example, about 13:1.

In further specific embodiments, the weight ratio between the (sum of the) first solubility-enhancing substance selected from the group of phospholipids and the second solubility-enhancing substance selected from the group of non-ionic surfactant on the one hand and CsA on the other hand is selected in the range of from about 5:1 to about 20:1, preferably from about 8:1 to about 12:1 and more preferably about 10:1.

In yet further specific embodiments, the weight ratio between the first solubility-enhancing substance selected from the group of phospholipids, preferably the lecithin, the the second solubility-enhancing substance selected from the group of nonionic surfactants, preferably the polysorbate and CsA is selected in the range of from about 15:1:1.5 to about 5:0.3:0.5, and preferably at about 9:0.7:1.

In specific embodiments, the compositions, or more specifically, the liquid compositions for use according to the present invention comprises cyclosporine A (CsA) in the form of liposomal cyclosporine A (L-CsA) or, in other words, in liposomally solubilized form. Accordingly, in specific embodiments, the liquid composition for use according to the present invention is a liposomal formulation. The liposomes comprising CsA, or in other words, the liposomal CsA (L-CsA) are formed primarily by the phospholipids contained in the composition and are preferably unilamellar liposomes. The liposomes preferably have an average diameter of at most about 100 nm measured as z-average using photon correlation spectroscopy with for example a Malvern ZetaSizer device, and a polydispersity index of at most about 0.5, preferably at most about 0.4 also as measured by photon correlation spectroscopy.

In specific embodiments, the liquid composition for use according to the present invention comprises an aqueous liquid vehicle. The liquid vehicle may comprise water and optionally one or more physiologically acceptable organic solvents, such as ethanol or propylene glycol. In preferred embodiments, however, the present pharmaceutical compositions, especially in form of liquid pharmaceutical compositions are free or substantially free of organic solvents, especially free of propylene glycol, or comprise only ethanol as an organic solvent.

The liquid composition for use according to the present invention can optionally be prepared by providing an aqueous solution or suspension of CsA in a suitable liquid carrier, preferably a suitable aqueous liquid carrier, and dissolving the CsA after addition of at least one phospholipid and at least one non-ionic surfactant as described above in form of liposomes.

In specific embodiments, the liquid composition for use according to the present invention can optionally be prepared from a corresponding solid formulation for reconstitution comprising mixing or contacting L-CsA with an aqueous solvent or vehicle immediately before inhalation. Accordingly, in a specific embodiment, the liquid composition comprising liposomal CsA (L-CsA) for use according to the present invention is prepared by reconstitution of liposomal cyclosporine A (L-CsA), preferably of L-CsA in lyophilized form.

The solid formulation for reconstitution comprising L-CsA can be prepared by any method suitable for removing the solvent from a liquid formulation. Preferred examples of methods for preparing such solid formulations or compositions, however, comprise freeze drying and spray drying. Preferably, freeze drying is used.

To protect the active ingredient during the drying process, it may be useful to incorporate lyoprotective and/or bulking agents, such as a sugar or a sugar alcohol, in particular sucrose, fructose, glucose, trehalose, mannitol, sorbitol, isomalt, or xylitol. Of these agents, sucrose is particularly preferred.

The portion of the solid composition comprising an effective amount of the active compound, namely CsA provided in the form of L-CsA (i.e. a unit dose) is preferably dissolvable or dispersible in the above-mentioned aqueous liquid vehicle. In specific embodiments, the aqueous liquid vehicle has a volume of not more than about 10 ml. Preferably, the effective amount or unit dose of CsA or L-CsA is dissolvable or dispersible in a volume of not more than about 5 ml, not more than about 4 ml, or even not more than about 3 ml of the aqueous liquid vehicle. The volume of the aqueous liquid vehicle required for reconstitution of the solid L-CsA formulation will depend on the dose of the active ingredient, as well as on the desired concentration. If a smaller dose is required for a therapeutic effect, a smaller volume of the aqueous liquid vehicle might be sufficient to dissolve or disperse the solid formulation comprising the L-CsA.

In specific embodiments, an aqueous solution is preferably used as the aqueous liquid vehicle for reconstitution. Accordingly, in preferred embodiments of the liquid compositions of the present invention, the aqueous liquid vehicle comprises saline.

In specific embodiments, a saline solution is used as the aqueous liquid vehicle, wherein the concentration of sodium chloride is adjusted in order to yield a liquid formulation which has a physiologically acceptable osmolality and tolerability after reconstitution. The osmolality of the liquid compositions for use according to the present inventions, in preferred embodiments is in the range of from about 450 to about 550 mOsmol/kg. A certain degree of hypo- and hyper-osmolality, however, may be generally still tolerated. The presence of permeant anions (such as chloride) in a concentration between 31 and 300 mM may improve tolerability (Weber et al. "Effect of nebulizer type and antibiotic concentration on device performance", Paediatric Pulmonology 23 (1997) 249-260). A hyperosmotic formulation can actually be preferred in certain applications. For example, the osmolality of a reconstituted liquid composition for use according to the present invention may range between 150 and 800 mOsmol/kg. Preferably, the aqueous liquid composition has an osmolality of about 250 to about 700 mOsmol/kg, or of about 250 to 600 mOsmol/kg. Most preferred, the aqueous liquid composition for use according to the present invention has an osmolality of about 400 to about 550 mOsmol/kg.

In specific embodiments, the liquid composition for use according to the present invention comprises an aqueous liquid vehicle that essentially consists of saline. In these specific embodiments as well as in other embodiments, in which the aqueous liquid vehicle comprises further constituents or solvents, the concentration of sodium chloride can range between about 0.1 and about 0.9% (w/v). Preferably, a saline solution with a sodium chloride concentration of about 0.25% (w/v) is used, wherein the term "w/v" means the weight of the dissolved sodium chloride per volume of the liquid vehicle comprised by the aqueous liquid composition.

In cases in which the liquid composition is prepared by reconstitution of a dried formulation, depending on the osmolality of the formulation before drying, the concentration of sodium chloride may also range between about 0.1 and about 0.9% (w/v). Preferably, a 0.25% (w/v) saline solution as described above is used.

When used for the preparation of the liquid compositions for use according to the present invention, the solid composition comprising CsA, preferably in the form of L-CsA, for reconstitution may be part of a pharmaceutical kit. Such kit preferably comprises the solid composition together with the liquid aqueous vehicle for reconstitution. Such a kit for preparation of liquid composition for administration as an aerosol is described in WO 03/035030.

After reconstitution, the CsA or, more specifically, the L-CsA formulation should have the same composition as before drying. In case the formulation is a liposomal formulation, it should also contain liposomes after reconstitution. Preferably, also the size of the liposomes is similar before drying and after reconstitution. With respect to the size of the liposomes, it is particularly preferred that the liposomes' size measured as z-average by photon correlation spectroscopy is between 40 and 100 nm, exhibiting a uniform size distribution (polydispersity index <0.4) after reconstitution with 0.25% (w/v) saline.

Surprisingly, it has been found that the liquid composition comprising especially liposomal cyclosporine A (L-CsA) as described above are useful in a method for the prevention of bronchiolitis obliterans syndrome (BOS) in a double lung transplanted patient or for the treatment of BOS or for the prevention or delay of the progression of BOS in a double lung transplanted patient being diagnosed with BOS, wherein the composition is administered to said patient by inhalation of said liquid composition in aerosolized form comprising a therapeutically effective dose of cyclosporine A (Cs-A).

According to the present invention, the bronchioliolitis obliterans syndrome (herein also referred to as "BOS") can be effectively prevented or treated, preferably treated, in double lung transplanted patients or the progression of BOS can be effectively prevented or delayed in patients who have received a double lung transplant (herein also referred to as "double lung transplanted patients") and who have been diagnosed with BOS, especially BOS 1 or BOS 2.

Surprisingly, when compared to patients having received a single lung transplant (herein also referred to as "single lung transplanted patients"), especially patients which are diagnosed with BOS, the treatment or, more specifically, the prevention or delay of the progression of the manifested BOS can be achieved more effectively in double lung transplanted patients. More specifically, a considerable delay or even prevention of a progression of a manifested BOS is obtained in double lung transplanted patients who inhale the liposomal cyclosporine A liquid formulation for use according to the present invention in addition to standard immunosuppressive therapy (hereinafter also referred to as "standard of care" or "SOC"). A comparable delay or prevention of BOS was not found within the same timeframe in a double lung transplanted population receiving standard immunosuppressive therapy alone or when compared to single lung transplanted patients, either when treated with the L-CsA containing compositions for use according to the present invention or when treated with SOC alone.

It should be noted, that the different effect of the inhaled cyclosporine composition for use according to the present invention in view of the type of transplantation (double versus single lung transplantation) was completely surprising and unexpected in view of earlier results of clinical studies as disclosed in WO 2016/146645.

According to the present invention, the liquid compositions comprising L-CsA are useful in a method for the prevention of bronchiolitis obliterans syndrome (BOS) in double lung transplanted patients, or for the treatment of BOS or for the prevention or delay of the progression of BOS in a double lung transplanted patient being diagnosed with BOS. In preferred embodiments, however, the liquid compositions comprising L-CsA for use according to the present invention are useful in a method for the treatment of bronchiolitis obliterans syndrome (BOS) or for the prevention or delay of the progression of BOS in a double lung transplanted patient being diagnosed with BOS. The existence of BOS can be determined on the basis of spirometric measurements of the forced expiratory volume (FEV). Preferably, the reduction of the forced expiratory volume in one second ($FEV_1$) is used as an indicator of the existence of BOS and, accordingly, for the risk of pulmonary chronic graft rejection. $FEV_1$ measurements can be performed according to current American Thoracic Society (ATS)/European Respiratory Society (ERS) spirometry guidelines. The forced expiratory volume in one second ($FEV_1$) is expressed in litre (L).

BOS is considered to exist when a sustained decrease in $FEV_1$ of at least 20% from the patient's maximum values in the absence of other causes occurs. BOS may be confirmed by at least two $FEV_1$ measurements which are at least three weeks apart. Maximal post-transplant values are the two best $FEV_1$ values taken at least three weeks apart. $FEV_1$ measurements should be sustained and measured at least three weeks apart. The administration of bronchodilators should be stopped prior to assessing $FEV_1$. It is assumed that decreases in $FEV_1$ due to causes other than chronic rejection such as acute rejection or lymphocytic bronchitis or infection will respond to appropriate medical management and that sustained irreversible declines in function are related to progression of chronic rejection and BOS.

Based on the percentage of decrease of $FEV_1$, BOS grading is possible (Estenne M, et al. Bronchiolitis obliterans syndrome 2001: an update of the diagnostic criteria. *J Heart Lung Transplant* 2002; 21 (3): 297-310). The following definitions and criteria can be applied:

BOS 0: $FEV_1$ >90% of baseline
BOS 0-p: $FEV_1$ 81% to 90% of baseline
BOS 1: $FEV_1$ 66% to 80% of baseline
BOS 2: $FEV_1$ 51% to 65% of baseline
BOS 3: $FEV_1$ 50% or less of baseline The compositions for use according to the present invention may be useful in a method for the treatment of BOS or for the prevention or delay of the progression of BOS in a double lung transplanted patient being diagnosed with BOS in general, namely of either grade of BOS such as BOS 0, BOS 0-p, BOS 1, BOS 2 or BOS 3 and preferably for BOS 1, BOS 2 or BOS 3. In specific embodiments, however, the liquid composition for use according to the present invention are especially useful for the treatment of double lung transplanted patients diagnosed with BOS 0-p or higher, preferably BOS 1 or BOS 2. In further specific embodiments, the liquid composition for use according to the present invention are especially useful for the treatment of double lung transplanted patients diagnosed with BOS 0-p or BOS 1.

Actually, to be able to treat both, single and double lung transplanted patients, as one population within a single study, the dose administered to single lung transplanted patients preferably is about half of the dose administered to double lung transplanted patients. Since the active compound CsA has a topical effect, it was expected that the same effect would be obtained with a dose reduced by half where the target surface was also reduced by half. In other words, it was expected that the same effect would be obtained in single and double lung transplanted patients when the dose was adjusted depending on the type of transplantation. Nevertheless, even when administering a comparable dose, the inventors surprisingly found that the effect of inhaled cyclosporine in the prevention or delay of the manifested BOS, especially BOS 1 or BOS 2 was much more pronounced in the double lung transplanted population.

It was surprisingly found that the compositions for use according to the present invention may prevent or significantly delay or reduce the progression of BOS, especially BOS 1 or BOS 2 once manifested and diagnosed after double lung transplantation when compared to conventional treatment with standard immunosuppressive therapy (SOC) alone or when compared to single lung transplanted patients.

Therefore, the CsA or L-CsA containing compositions for use according to the present invention used in the treatment of double lung transplanted patients may contribute significantly to extend and maximize the survival probability and survival time for patients who are at risk to develop or who have developed BOS, more specifically BOS 1 or BOS 2 after double lung transplantation and therefore to reduce or minimize the development or progression of chronic pulmonary graft rejection. The composition for use according to the present invention can be administered according to a pre-determined dosing regimen. More specifically, the composition can be administered to the double lung transplanted patient a specific number of times during each week of treatment. For example, the composition can be administered three times per week. In preferred embodiments, the composition for use according to the present invention is administered daily. In a specific embodiment, the composition for use according to the present invention is administered to said double lung transplanted patient at risk to develop BOS or being diagnosed with BOS twice or even several times daily.

The composition, preferably the liquid composition for use according to the present invention preferably has a CsA concentration in the range of from about 0.5 to about 10 mg/mL, or in other words the liquid composition comprises CsA in the form of L-CsA at a concentration from about 0.5 to about 10 mg/mL, preferably from about 1 to about 6 mg/mL, and more preferably of from about 1 up to about 5 mg/mL. Most preferred, the composition for use according to the present invention contains CsA (in the form of L-CsA) at a concentration of about 4 mg/mL.

The volume of a unit dose of the composition for use according to the present invention is preferably low in order to allow short nebulization times. The volume, also referred to as the "volume of a dose", or a "dose unit volume", or a "unit dose volume", should be understood as the volume which is intended for being used for one single administration. A unit dose is defined as the dose of CsA (in the form of L-CsA) in the composition, more specifically the liquid composition, filled in the nebulizer for one single administration. Specifically, the volume of a unit dose may be less than 10 mL. Preferably, the volume is in the range from about 0.3 to about 3.5 mL, more preferably about 1 to about 3 mL. For example, the volume is about 1.25 mL or about 2.5 mL. In case the composition is obtained after reconstitution, the volume of the liquid vehicle, preferably the aqueous liquid vehicle or even more preferably the saline solution for reconstitution should be adapted according to the desired volume of the reconstituted composition.

The therapeutically effective unit dose of CsA comprised by the composition for use according to the present invention preferably ranges from about 1 mg to about 15 mg for single lung transplanted patients per day. Most preferred, an effective unit dose of about 10 mg CsA per day can be applied in single lung transplanted patients. Such doses were found to be well tolerated by double lung transplanted patients at risk to develop or being diagnosed with BOS.

The therapeutically effective daily dose of CsA to be administered to double lung transplanted patients being diagnosed with BOS can range between 2 mg and 30 mg. Accordingly, in preferred embodiments, CsA is administered at an effective daily dose in the range of 2 to 30 mg or at an effective daily dose in the range of 5 to 30 mg. In a preferred embodiment, an effective daily dose of about 20 mg CsA can be administered to double lung transplanted patients being at risk to develop or being diagnosed with BOS. It should be understood that in cases in which CsA is administered in form of L-CsA all amounts as outlined above refer to the amount of CsA contained in the liposomes.

The compositions or, more preferably, the liquid compositions for use according to the present invention may advantageously be aerosolized and administered by a nebulizer able to convert a solution, colloidal formulation or suspension such as the present compositions comprising CsA in the form of L-CsA, into a high fraction of droplets which are able to reach the periphery of the lungs. Practically, a jet nebulizer, ultrasonic nebulizer, piezoelectric nebulizer, electro-hydrodynamic nebulizer, membrane nebulizer, electronic membrane nebulizer, or electronic vibrating membrane nebulizer may be used. Examples of suitable nebulizers include the SideStream® (Philips), AeroEclipse® (Trudell), LC Plus® (PARI), LC Star® (PARI), LC Sprint® (PARI), I-Neb® (Philips/Respironics), IH50 (Beurer), MicroMesh® (Health & Life, Schill), Micro Air® U22

(Omron), Multisonic® (Schill), Respimat® (Boehringer), eFlow® (PARI), AeroNebGo® (Aerogen), AeroNeb Pro® (Aerogen), and AeroDose® (Aerogen) device families.

Preferably however, especially in cases in which liquid compositions comprising L-CsA are to be nebulized, a piezoelectric nebulizer, electro-hydrodynamic nebulizer, membrane nebulizer, electronic membrane nebulizer, or electronic vibrating membrane nebulizer may be used. In these cases, suitable nebulizers comprise the INeb® (Philips/Respironics), IH50 (Beurer), MicroMesh® (Health & Life, Schill), Micro Air® U22 (Omron), Multisonic® (Schill), Respimat® (Boehringer), eFlow® (PARI), AeroNebGo® (Aerogen), AeroNeb Pro® (Aerogen), and AeroDose® (Aerogen) device families. In preferred embodiments, for targeting the drug CsA, either as such or in form of liposomal CsA (L-CsA), to the lower respiratory tract, the composition for use according to the present invention is aerosolized with an electronic vibrating membrane nebulizer. In a particularly preferred embodiment, the liquid composition for use according to the present invention is aerosolized with an eFlow® neblizer (PARI Pharma GmbH).

The eFlow® nebulizer nebulizes liquid drug formulations, such as the compositions of the present invention, with a perforated vibrating membrane resulting in an aerosol with a low ballistic momentum and a high percentage of droplets in a respirable size range, usually below 5 μm. The eFlow® nebulizer is designed for a more rapid and efficient nebulization of medication due to a higher nebulization rate, lower drug wastage and a higher percentage of drug available as delivered dose (DD) and respirable dose (RD) compared to conventional nebulizers such as jet nebulizers.

Preferably, a suitable nebulizer, specifically a vibrating membrane nebulizer, can deliver such a unit dose at a rate of at least about 0.1 mL/min or, assuming that the relative density of the composition will normally be around 1, at a rate of at least about 100 mg/min. More preferably, the nebulizer is capable of generating an output rate of at least about 0.15 mL/min or 150 mg/min, respectively. In further embodiments, the output rates of the nebulizer are at least about 0.2, 0.3, 0.4, 0.5, 0.6, 0.7, 0.8, 0.9 or 1 mL/min.

Furthermore, the output rate of the nebulizer should be selected to achieve a short nebulization time of the liquid composition. Obviously, the nebulization time will depend on the volume of the composition which is to be aerosolized and on the output rate. Preferably, the nebulizer should be selected or adapted to be capable of aerosolizing a volume of the liquid composition comprising an effective dose of the active compound within not more than about 20 minutes. More preferably, the nebulization time for a unit dose is not more than about 10 minutes. Even more preferred, the nebulization time for a unit dose is not more than about 5 min.

In addition to providing a high delivered dose and having short nebulization times, the nebulizer for administering CsA in the form of L-CsA is preferably constructed in such way that contamination of the environment with CsA is inhibited. For this purpose, a filter device can be placed on the exhalation valve of the nebulizer.

In a preferred embodiment, the nebulizer comprises features for monitoring for example the time, date and duration of inhalation by the patient. An example of such features is a chip card on which the nebulization time and duration are recorded.

Alternatively, wireless transmission of such data to a cloud and/or server can be applied. This enables medical staff to check patient adherence. The monitoring system may comprise a nebulizer such as the ones described above, controller, server, databank, cloud, provider, physician, health insurance company and/or telephone service.

It has been found that an adherence of at least 65%, or of at least 75% is beneficial for obtaining a relevant prevention or delay of the progression of BOS in double lung transplanted patients. To reach an adherence of at least 65%, the double lung transplanted patient at risk to develop or being diagnosed with BOS, specifically BOS 1 or BOS 2, must inhale the formulation as intended in at least 65% of the intended inhalation cycles. On the basis of a twice daily inhalation regimen, for example, this means that the patient is not allowed to miss more than 39 inhalations in a period of 8 weeks, which is equivalent to approximately 5 inhalations per week. Any inhalation that is omitted, that is not performed until the complete unit dose is inhaled or that is deficient for any other reason is considered to be a "missed" inhalation, or in other words an inhalation which is not "as intended". More preferably, the formulation for use according to the present invention is inhaled with an adherence of at least 75%, i.e. the patient must inhale the formulation as intended in at least 75% of the intended inhalation cycles on the basis of a twice daily inhalation regimen. This is reached when no more than 28 inhalations are missed in a period of 8 weeks, or approximately 3.5 inhalations per week.

In another embodiment, the features for recording the nebulization time, date and duration are connected with a system which generates a signal as soon as the inhalation is not performed timely and correctly in a predetermined number of inhalation cycles. Due to the use of such monitoring systems, either without or with systems generating a signal, it can be assured that patients use the nebulizer device correctly. The system for generating the signal may include, for example, detection by a sensor of, for example, the presence of a fluid in the fluid reservoir, the measurement of the inhalation flow, inhalation time, inhalation duration, and/or inhalation volume. Visual, audible or sensory feedback can be given, for example, on the relevant patient behavior and use factors affecting therapy or on the diagnosis of the application. This feedback may include information to improve the patient adherence to a defined medical treatment protocol and/or the CsA deposition and distribution in the lungs.

In embodiments where for example the time, date and duration of each inhalation is recorded on features for monitoring, it is possible to continuously monitor the patient. In the embodiment where the monitoring system is connected with a system generating a signal, the inhalation behavior of the patient can be corrected as soon as the adherence of the patient decreases below a predefined adherence limit. The signal can be a signal generated by the nebulizer itself but can also be a signal generated on a remote device, which e.g. notifies the patient's medical practitioner. Upon being notified of the lack of adherence, the medical practitioner can contact the patient in order to remind the patient that proper inhalation is a prerequisite for a successful prevention of pulmonary chronic graft rejection.

The inventors have found that monitoring is useful in lung transplanted patients, and especially in double lung transplanted patients, since the effect of a liquid L-CsA composition inhaled formulation is more pronounced in compliant patients.

Furthermore, it has been found advantageous to administer the composition for use according to present invention to the double lung transplanted patient being at risk to develop or being diagnosed with BOS over prolonged periods of time, such as over periods of at least 2 weeks, or at least 4 weeks, or at least 8 weeks, or at least 12 weeks, or at least 16 weeks, or at least 20 weeks or even longer. In particularly preferred embodiments, the liquid composition for use according to the present invention is administered over a period of at least 24 weeks, or even 36, or even 48 weeks, or even longer such as 12 months, 24 months, 36 months or even years, such as 4 years or 5 years or even 6 years, in case this may be indicated to prevent BOS or to delay or reduce the progression of BOS, specifically BOS 1 or BOS 2 in a double lung transplanted patient.

In further preferred embodiments, the administration of the compositions for use according to the present invention is performed on a continuous daily basis, preferably once or even more, preferably twice daily over a period of at least 24 weeks, preferably of at least 48 weeks.

In a further embodiment, the inhaled CsA composition of the present invention is used in combination with one or more active ingredients used in standard immunosuppressive therapy after lung transplantation. Accordingly, in preferred embodiments, the liquid composition for use according to the present invention is characterized in that the double lung transplanted patient is co-treated with standard immunosuppressive therapy (herein also referred to as "SOC").

In standard immunosuppressive therapy after lung transplantation one or more active ingredients of the groups of immunosuppressants and corticosteroids can be administered. Examples of immunosuppressants are compounds belonging to the groups of immunoglobulins (antibodies), cell-cycle inhibitors (anti-metabolites/anti-proliferatives), such as azathioprine and mycophenolic acid and its salts, and calcineurin inhibitors, such as cyclosporine, tacrolimus, or mTOR inhibitors such as sirolimus and everolimus. Examples of corticosteroids are compounds belonging to the group of hydrocortisone, methylprednisolone, prednisone, and any of their salts, esters and derivatives.

In specific embodiments, the composition for use according to the invention is used in combination with one or more active ingredients selected from the group consisting of tacrolimus, mycophenolate mofetil and/or corticosteroids, preferably in an oral standard immunosuppressive therapy. Accordingly, in specific embodiments, the composition for use according to the present invention is administered in combination with standard immunosuppressive therapy comprising administration of one or more active ingredients selected from the group consisting of tacrolimus or cyclosporine; mycophenolate mofetil or sirolimus; and corticosteroids.

In further specific embodiments, the composition for use according to the present invention is used in combination with a triple drug therapy, where a combination of a calcineurin inhibitor, a cell-cycle inhibitor and a corticosteroid is administered. Preferably, the calcineurin inhibitor is tacrolimus, the cell-cycle inhibitor is mycophenolate mofetil and the corticosteroid is prednisone. The active ingredients used in combination with the composition according to the invention are preferably administered orally. In these cases of standard immunosuppressive therapy, tacrolimus is usually administered in an amount to achieve a whole blood through level (WBTL) of 8 to 12 ng/ml, preferably in an amount of about of 0.06 mg/kg (with regard to the body mass of the treated patient). Furthermore, mycophenolate mofetil in standard immunosuppressive therapy is administered typically in an amount of from about 1 g, sometimes up to 3 g, preferably of about 1 g. Prednisone when used under standard immunosuppressive therapy is typically administered in an amount of from about 20 to about 25 mg/day, preferably of about 20 mg/day.

As a consequence, the usual dose of active ingredients used in standard immunosuppressive therapy can be reduced when a cyclosporine liquid composition for inhalation according to the present invention is used in combination with these ingredients. In other words, the dose which is generally required for successful immunosuppression when not using inhaled CsA or, more specifically, L-CsA—which is herein defined as the usual dose—can often be reduced. This is advantageous since the use of systemically administered immunosuppressants can lead to considerable adverse effects, which are generally dose dependent.

The compositions for use according to the present invention allow for the effective treatment or the prevention of BOS in double lung transplanted patients or for the effective delay of the progression of BOS in double lung transplanted patients being diagnosed with BOS. As mentioned earlier, the reduction of the forced expiratory volume in one second ($FEV_1$) can be used as an indicator for the existence of BOS and, accordingly, for the risk of pulmonary chronic graft rejection. Accordingly, in specific embodiments, the compositions for use according to the present invention are useful for the treatment of BOS, especially BOS 1 or BOS 2, in double lung transplanted patients, wherein the progression of BOS of the double lung transplanted patient is substantially prevented or is reduced to a level of up to 50%, or of up to 40%, or of up to 30%, or of up to 20% or even of up to 15% or 10% or even of up to 5% decline of the forced expiratory volume in one second ($FEV_1$) of said patient compared to the $FEV_1$-value of said patient at the begin of the treatment, or the begin of the randomization or the begin of the study, respectively. In preferred embodiments, the progression of BOS, especially BOS 1 or BOS 2, of the double lung transplanted patient is substantially prevented or reduced to a level of up to 20% decline of the forced expiratory volume in one second ($FEV_1$) of said patient compared to the $FEV_1$-value of said patient at the begin of the treatment, or the begin of the randomization or the begin of the study, respectively.

This effect may be achieved by the treatment of the double lung transplanted patent being at risk to develop or being diagnosed with BOS with the compositions of the present invention or according to the methods of the present invention for a prolonged period of time, such as for at least 2 weeks, or at least 4 weeks, or at least 8 weeks, or at least 12 weeks, or at least 16 weeks, or at least 20 weeks or even longer such as at least 24 weeks, or even 36, or even 48 weeks, or even longer such as 12 months, 24 months, 36 months or even years, such as 4 years or 5 years or even 6 years, in case this may be indicated to prevent, delay or reduce the progression of BOS, specifically BOS 1 or BOS 2 in a double lung transplanted patient.

In further preferred embodiments, the progression of BOS of the double lung transplanted patient is substantially prevented or reduced to a level of up to 20%, preferably of up to 10% decline of the forced expiratory volume in one second ($FEV_1$) of said patient compared to the $FEV_1$-value of said patient at the begin of the treatment, or the begin of the randomization or the begin of the study, respectively, after treatment of said double lung transplanted for a period of at least 24 weeks of treatment with the compositions for use according to the present invention followed by at least 24 weeks without treatment.

Furthermore, it has been found that the compositions for use according to the present invention allow for the significant extension of event-free survival of double lung transplanted patients being at risk to develop or being diagnosed with BOS, preferably being diagnosed with BOS, wherein the event-free survival is characterized as the survival time in which the double lung transplanted patient does not experience either a decline in $FEV_1$ of at least 20% and/or the need for re-transplantation or death.

The compositions for use according to the present invention, furthermore, allow for the significant extension of the event-free survival probability in double lung transplanted patients being at risk to develop or being diagnosed with BOS, especially BOS 1 or BOS 2. Accordingly, in preferred embodiments the composition for use according to the present invention allows for the treatment of double lung transplanted patients being at risk to develop or being diagnosed with BOS, wherein the event-free survival probability is at least 50%, or at least 60%, or at least 70%, or at least 80%, or even at least 90% after a period of at least 12 or at least 24 or at least 36 or even after at least 48 weeks or even longer such as 12 months, 24 months, 36 months or even years, such as 4 years or 5 years or even 6 years from the beginning of the treatment, wherein the event is selected from a decline in $FEV_1$ of at least 10% or at least 20% and/or need for re-transplantation or death. In preferred embodiments, the event-free survival probability for double lung transplanted patients being at risk to develop or being diagnosed with, preferably diagnosed with BOS is at least 60%, preferably at least 80% after at least 24 weeks of treatment with the compositions for use according to the present invention followed by at least 24 weeks without treatment.

In further embodiments, the risk to experience an event selected from a decline in $FEV_1$ of at least 10% or at least 20%, need for re-transplantation and/or death within a prolonged period of time, such as at least 2 weeks, or at least 4 weeks, or at least 8 weeks, or at least 12 weeks, or at least 16 weeks, or at least 20 weeks or even longer such as at least 24 weeks, or even 36, or even 48 weeks, or even longer such as 12 months, 24 months, 36 months or even years, such as 4 years or 5 years or even 6 years, preferably however within 48 weeks from the begin of the treatment for a double lung transplanted patient at risk to develop or being diagnosed with BOS may be reduced significantly.

Accordingly, the composition for use according to the present invention allows for the treatment of double lung transplanted patients being at risk to develop or being diagnosed with BOS, wherein the risk to experience an event selected from a decline in $FEV_1$ of at least 20%, need for re-transplantation and/or death (Event-free survival probability) within a prolonged period of time such as at least 2 weeks, or at least 4 weeks, or at least 8 weeks, or at least 12 weeks, or at least 16 weeks, or at least 20 weeks or even longer such as at least 24 weeks, or even 36, or even 48 weeks, or even longer such as 12 months, 24 months, 36 months or even years, such as 4 years or 5 years or even 6 years, preferably at least 48 weeks from the beginning of the treatment for the double lung transplanted patient treated with the composition of the present invention in aerosolized form comprising CsA or preferably L-CsA is reduced by at least 30% (abs.), preferably by at least 35% (abs.) compared to the risk to experience a corresponding event under treatment with standard immunosuppressive therapy (SOC) alone.

In preferred embodiments, the risk to experience an event selected from a decline in $FEV_1$ of at least 20%, need for re-transplantation and/or death as described above is reduced by at least 30%, preferably by at least 35% (abs.), especially after at least 24 weeks of treatment with the compositions for use according to the present invention followed by at least 24 weeks without treatment.

A further measure to determine the potential prevention or delay of progression of BOS in a double lung transplanted patient is the determination of the mean monthly change or, more specifically, the monthly loss or decline in $FEV_1$ ($\Delta FEV_1$/month, hereinafter also referred to as "$FEV_1$-slope") as determined for such patient on the basis of $FEV_1$ measurements conducted on a regular and repeated basis over a prolonged period of time as described above, such as over a period of at least 12 or at least 24 or at least 36 or even after at least 48 weeks or 12 months or even 24 or 36 months or even longer such 4 years, or 5 years or even 6 years, preferably over a 48-week period. Accordingly, in preferred embodiments the composition for use according to the present invention allows for the treatment of double lung transplanted patients being at risk to develop or being diagnosed with BOS wherein the monthly change in $FEV_1$ ($\Delta FEV_1$/month) remains substantially constant or has a value in the range of from about 0 to about 0.055 L/month (corresponding to a loss or decline in $FEV_1$ of up to 0.055 L/month) or of from about 0 to about 0.05 L/month or from about 0 to about 0.045 L/month about 0 to about 0.04 L/month. In preferred embodiments, the composition for use according to the present invention allows for the treatment of double lung transplanted patients being at risk to develop or being diagnosed with BOS wherein the monthly change in $FEV_1$ ($\Delta FEV_1$/month) remains substantially constant or has a value in the range of from about 0 to about 0.04 L/month, meaning a monthly loss of $FEV_1$ in the range of about 0 to about 0.04 L.

A yet further measure to determine the potential delay or progression of BOS in a double lung transplanted patient being at risk to develop or being diagnosed with BOS is the determination of the absolute change, or more specifically, the absolute loss in $FEV_1$ ($\Delta FEV_1$/abs.) as determined for such patient on the basis of $FEV_1$ measurements conducted at the beginning of the treatment and at the end of the treatment, specifically after a prolonged period of time such as over a period of at least 12 weeks or at least 24 weeks or at least 36 weeks or even after at least 48 weeks or 12 months or even 24 or 36 months or even longer 4 years, or 5 years or even 6 years, preferably over a 48-week period. Accordingly, in specific embodiments, the composition for use according to the present invention allows for the treatment of double lung transplanted patients being at risk to develop or being diagnosed with BOS, wherein the absolute change in $FEV_1$ ($\Delta FEV_1$/abs.) between baseline (beginning of the treatment) and the end of the treatment period, such as week 48 after the beginning of the treatment, of the double lung transplanted patient being at risk to develop or being diagnosed with BOS is not more than 350 mL, meaning an overall loss of $FEV_1$ of said patient of not more than 350 mL, preferably not more than 300, or 250, or 200 or even 150 mL. In further embodiments, the absolute change in $FEV_1$ ($\Delta FEV_1$/abs.) between baseline (beginning of the treatment) and the end of the treatment period, such as week 48 after the beginning of the treatment of the double lung transplanted patient being at risk to develop or being diagnosed with, preferably being diagnosed with BOS, is in the range of 150 to 350 ml.

A yet further measure to determine the potential delay or progression of BOS in a double lung transplanted patient being at risk to develop or being diagnosed with BOS and being treated with the compositions for use according to the present invention is the determination of the relative change, or more specifically, the relative loss in $FEV_1$ ($\Delta FEV_1$/rel.)

relative to the loss of $FEV_1$ in a patient treated with standard immunosuppressive therapy (SOC) alone, specifically after a prolonged period of treatment time such as such as over a period of at least 12 or at least 24 or at least 36 or even after at least 48 weeks or 12 months or even 24 or 36 months or even longer 4 years, or 5 years or even 6 years, preferably over a 48-week period. Accordingly, in specific embodiments, the composition for use according to the present invention allows for the treatment of double lung transplanted patients being diagnosed with BOS, wherein the relative change or difference in $FEV_1$ ($\Delta FEV_1$/rel.) in a double lung transplanted patient treated with the compositions comprising L-CsA for use according to the present invention compared to the loss of $FEV_1$ in a patient treated with standard immunosuppressive therapy (SOC) alone is at least 200 mL, or at least 250 mL, or at least 300 mL or even more, such as at least 350 mL or at least 400 mL after a period of at least 12 or at least 24 or at least 36 or even after at least 48 weeks or 12 months or even 24 or 36 months or even longer 4 years, or 5 years or even 6 years, preferably over a 48-week period after the beginning of the treatment.

In preferred embodiments, the composition comprising L-CsA for use according to the present invention allows for the treatment of double lung transplanted patients being at risk to develop or being diagnosed with BOS, wherein the relative loss or difference in $FEV_1$ ($\Delta FEV_1$/rel.) relative to the loss of $FEV_1$ in a patient treated with standard immunosuppressive therapy (SOC) alone is in the range of from about 200 to about 400 mL after 48 weeks from the beginning of the treatment. This means that, for example, according to these preferred embodiments, after a period of 48 weeks a patient treated with the compositions according to the present invention has an $FEV_1$-value which is from about 200 to about 400 mL higher than the $FEV_1$-value of a double lung transplanted patient being treated with standard immunosuppressive therapy alone.

The composition for use according to the present invention may be particularly useful for the successful treatment of those double lung transplanted patients being at risk to develop or being diagnosed with BOS which have not been diagnosed with airway stenosis prior to the begin of the treatment, and especially for those who have, furthermore, not been diagnosed with airway stenosis at week 24 after begin of the treatment, as ascertained by bronchoscopy with bronchoalveolar lavage (BAL)).

Furthermore, the composition for use according to the present invention may be particularly useful for the successful treatment of those double lung transplanted patients being at risk to develop or being diagnosed with BOS which have not been diagnosed with an untreated infection prior to the begin of the treatment, and especially for those who have, furthermore, not been diagnosed with an untreated infection at week 24 after begin of the treatment.

The composition comprising CsA, specifically L-CsA for use according to the present invention, is to be inhaled in aerosolized form. This, however, may help to reduce the systemic exposure of the patient to large extend. Accordingly, the composition for use according to the present invention, furthermore, allows for the treatment of double lung transplanted patients being at risk to develop or being diagnosed with BOS, wherein the mean blood concentration of CsA in the double lung transplanted patient treated with the liquid composition comprising CsA by inhalation is up to 100 ng/ml, preferably up to 60 ng/ml.

In a further aspect, the present invention provides for the use of a composition comprising cyclosporine A (CsA) in the preparation of a medicament for the prevention or treatment of bronchiolitis obliterans syndrome (BOS) in a double lung transplanted patient or for the prevention or delay of the progression of BOS in a double lung transplanted patient being diagnosed with BOS, wherein the composition is administered to said patient by inhalation of said composition in aerosolized form comprising a therapeutically effective dose of CsA. As outlined above in connection with the compositions of the first aspect of the invention, the compositions comprising CsA may be used in solid or liquid form for the preparation of the medicament according to this aspect of the invention. In case solid compositions are used, they may be reconstituted with a suitable liquid vehicle or solvent as described in detail above. I addition to this, all features disclosed and described above in connection with the compositions for use according to the first aspect of the invention can also be applied to the use of such compositions according to this aspect of the invention.

In yet a further aspect, the present invention provides for a method for preventing bronchiolitis obliterans syndrome (BOS) in a double lung transplanted patient, or for treating BOS or for preventing or delaying the progression of BOS in a double lung transplanted patient being diagnosed with BOS, the method comprising the steps of
  (a) identifying a patient who has received a double lung transplant and is at risk to develop or has subsequently developed BOS; and
  (b) administering to said patient a therapeutically effective dose of aerosolised cyclosporin A (CsA) by inhalation.

It should be pointed out, that also for the method according to this aspect of the invention, all features disclosed and described above in connection with the compositions for use according to the first aspect of the invention can also be applied to the method for preventing bronchiolitis obliterans syndrome (BOS) in a double lung transplanted patient or for treating BOS or for preventing or delaying the progression of BOS in a double lung transplanted patient being diagnosed with BOS according to this aspect of the invention.

For the avoidance of doubt, however, the following is a list of numbered embodiments of the composition comprising cyclosporine A (CsA), specifically liposomal CsA (L-CsA) for use in the prevention of bronchiolitis obliterans syndrome (BOS) in a double lung transplanted patient or for the prevention or delay of the progression of BOS in a double lung transplanted patient being diagnosed with BOS according to the present invention which are also comprised by the method for preventing bronchiolitis obliterans syndrome (BOS) in a double lung transplanted patient or for treating BOS or for preventing or delaying the progression of BOS in a double lung transplanted patient being diagnosed with BOS according to this aspect of the invention:

1. A composition comprising cyclosporine A (CsA) for use in the prevention of bronchiolitis obliterans syndrome (BOS) in a double lung transplanted patient, or for the treatment of BOS or for the prevention or delay of the progression of BOS in a double lung transplanted patient being diagnosed with BOS, wherein the composition is administered to said patient by inhalation of said composition in aerosolized form comprising a therapeutically effective dose of cyclosporine A.
2. A composition comprising cyclosporine A (CsA) for use according to item 1, in the treatment of bronchiolitis obliterans syndrome (BOS) or for the prevention or delay of the progression of BOS in a double lung transplanted patient being diagnosed with BOS, wherein the composition is administered to said patient by inhalation of said composition in aerosolized form comprising a therapeutically effective dose of cyclosporine A.
3. The composition for use according to item 1 or 2, wherein the double lung transplanted patient is diagnosed with BOS 1 or BOS 2.
4. The composition for use according to any preceding item, wherein the composition comprises cyclosporine A in the form of liposomal cyclosporine A (L-CsA).
5. The composition for use according to any preceding item, wherein the composition is a liquid composition.
6. The composition for use according to item 5, wherein the composition comprises an aqueous liquid vehicle.
7. The composition for use according to item 6, wherein the aqueous liquid vehicle comprises saline.
8. The composition for use according to item 6 or 7, wherein the aqueous liquid vehicle essentially consists of saline, preferably of saline with a concentration of 0.25%.
9. The composition for use according to any preceding item, wherein the liquid composition has a CsA concentration in the range of from 0.5 to 10 mg/mL.
10. The composition for use according to any preceding item, wherein the liquid composition is prepared by reconstitution of liposomal cyclosporine A in lyophilized form.
11. The composition for use according to any preceding item, wherein cyclosporine A is administered at an effective daily dose in the range of 5 to 30 mg.
12. The composition for use according to any preceding item, wherein cyclosporine A is administered at an effective daily dose of 20 mg.
13. The composition for use according to any preceding item, wherein the composition is administered to said patient twice daily.
14. The composition for use according to any preceding item, wherein the composition is administered over a period of at least 24 weeks.
15. The composition for use according to any preceding item, wherein the double lung transplanted patient is co-treated with standard immunosuppressive therapy.
16. The composition for use according to item 15, wherein the standard immunosuppressive therapy comprises administration of one or more active ingredients selected from the group consisting of tacrolimus or cyclosporine; mycophenolate mofetil or sirolimus; and corticosteroids.
17. The composition for use according to item 15 or 16, wherein the standard immunosuppressive therapy comprises oral administration of tacrolimus, mycophenolate mofetil and prednisone.
18. The composition for use according to any one of items 15 to 17, wherein tacrolimus is administered in an amount of 0.06 mg/kg.
19. The composition for use according to any one of items 15 to 18, wherein mycophenolate mofetil is administered in an amount of 1 g.
20. The composition for use according to any one of items 15 to 19, wherein prednisone is administered in an amount of about 20 to about 25 mg/day.
21. The composition for use according to any preceding item, wherein the formulation is aerosolized with an electronic vibrating membrane nebulizer.
22. The composition for use according to any preceding item, wherein the formulation is aerosolized with an eFlow® nebulizer.
23. The composition for use according to any preceding item, wherein the progression of BOS of the double lung transplanted patient being diagnosed with BOS is prevented or reduced to a level of up to 20% decline of the forced expiratory volume in one second ($FEV_1$) of said patient compared to $FEV_1$-value at the begin of the treatment.
24. The composition for use according to any preceding item, wherein the event-free survival probability of the double lung transplanted patient being diagnosed with BOS is at least 60% after at least 48 weeks from the begin of the treatment, wherein the event is selected from a decline in $FEV_1$ of at least 20%, need for re-transplantation and/or death.
25. The composition for use according to any preceding item, wherein the risk to experience an event selected from a decline in $FEV_1$ of at least 20%, need for re-transplantation and/or death within a period of at least 48 weeks from the beginning of the treatment for the double lung transplanted patient treated with the composition of the present invention in aerosolized form comprising CsA is reduced by at least 30% (abs.), preferably by at least 35% (abs.) compared to the risk to experience a corresponding event under treatment with standard immunosuppressive therapy (SOC) alone.
26. The composition for use according to any preceding item, wherein the mean monthly change in $FEV_1$ ($\Delta FEV_1$/month) of the double lung transplanted patient being diagnosed with BOS remains substantially constant or has a value in the range of from about 0 to about 0.04 L/month.
27. The composition for use according to any preceding item, wherein the absolute change in $FEV_1$ ($\Delta FEV_1$/abs.) between baseline (beginning of the treatment) and the end of the treatment period of the double lung transplanted patient being diagnosed with BOS is not more than 350 mL.
28. The composition for use according of any preceding claim, wherein the relative loss in $FEV_1$ ($\Delta FEV_1$/rel.) of the double lung transplanted patient being diagnosed with BOS relative to the loss of $FEV_1$ in a patient treated with standard immunosuppressive therapy (SOC) alone is at least 200 mL.
29. The composition for use according to any preceding item, wherein the double lung transplanted patient has not been diagnosed with airway stenosis prior to the begin of the treatment, and preferably at week 24 after begin of the treatment, as ascertained by bronchoscopy with with bronchalveolar lavage (BAL).
30. The composition for use according to any preceding item, wherein the double lung transplanted patient being diagnosed with BOS has not been diagnosed with an untreated infection prior to randomization, and preferably at week 24 after begin of the treatment.
31. The composition for use according to any preceding item, wherein the maximum blood concentration of CsA in the double lung transplanted patient being diagnosed with BOS and being treated with the liquid composition comprising CsA is up to 100 ng/ml, preferably up to 60 ng/ml.
32. The composition for use according to item 21 or 22, wherein the nebulizer can deliver a unit dose at a rate of at least about 0.1 mL/min.
33. A method for preventing bronchiolitis obliterans syndrome (BOS) in a double lung transplanted patient, or for treating BOS or for preventing or delaying the progression of BOS in a double lung transplanted patient being diagnosed with BOS, the method comprising the steps of
  (a) identifying a patient who has received a double lung transplant and is at risk to develop or subsequently has developed BOS; and
  (b) administering to said patient a therapeutically effective dose of aerosolised cyclosporin A (CsA) by inhalation.
34. A method according to item 33 for treating bronchiolitis obliterans syndrome (BOS) in a double lung transplanted patient or for preventing or delaying the progression of BOS in a double lung transplanted patient being diagnosed with BOS, the method comprising the steps of
  (a) identifying a patient who has received a double lung transplant and subsequently has developed BOS; and
  (b) administering to said patient a therapeutically effective dose of aerosolised cyclosporin A (CsA) by inhalation.
35. The method according to item 33 or 34, wherein the double lung transplanted patient is diagnosed with BOS 1 or BOS 2 (BOS grade I or II).
36. The method according to item 33 or 34, wherein the CsA is administered in form of an aerosolized composition comprising liposomal cyclosporine A (L-CsA).
37. The method according to item 33, wherein the CsA is administered in form of an aerosolized liquid composition comprising cyclosporine A (CsA).
38. The method according to item 33, wherein CsA is administered in the form of liposomal cyclosporine A (L-CsA).
39. The method according to item 36, wherein the composition further comprises an aqueous liquid vehicle.
40. The method according to item 39, wherein the aqueous liquid vehicle comprises saline.
41. The method according to item 39 or 40, wherein the aqueous liquid vehicle essentially consists of saline, preferably of saline with a concentration of 0.25% (w/v).
42. The method according to item 37, wherein the liquid composition has a CsA concentration in the range of from 0.5 to 10 mg/mL.
43. The method according to item 38, wherein the liquid composition is prepared by reconstitution of liposomal cyclosporine A (L-CsA) in lyophilized form.
44. The method according to item 33, wherein cyclosporine A is administered at an effective daily dose in the range of 5 to 30 mg.
45. The method according to item 33, wherein cyclosporine A is administered at an effective daily dose of 20 mg.
46. The method according to item 33, wherein the composition is administered to said patient twice daily.
47. The method according to item 33, wherein CsA is administered over a period of at least 24 weeks.
48. The method according to item 33, wherein the double lung transplanted patient is co-treated with standard immunosuppressive therapy.
49. The method according to item 48, wherein the standard immunosuppressive therapy comprises administration of one or more active ingredients selected from the group consisting of tacrolimus or cyclosporine; mycophenolate mofetil or sirolimus; and corticosteroids.
50. The method according to item 48, wherein the standard immunosuppressive therapy comprises oral administration of tacrolimus, mycophenolate mofetil and prednisone.
51. The method according to item 49 or 50, wherein tacrolimus is administered in an amount of 0.06 mg/kg.
52. The method according to items 49 or 50, wherein mycophenolate mofetil is administered in an amount of 1 g.
53. The method according to items 49 or 50, wherein prednisone is administered in an amount of 20 mg/day.
54. The method according to item 33, wherein the formulation is aerosolized with an electronic vibrating membrane nebulizer.
55. The method according to item 33, wherein the formulation is aerosolized with an eFlow® nebulizer.
56. The method according to item 36, wherein the formulation is inhaled with an adherence of at least 75%.
57. The method according to item 33, wherein the progression of BOS of the double lung transplanted patient being at risk to develop or being diagnosed with BOS is prevented or reduced to a level of up to 20% decline of the forced expiratory volume in one second ($FEV_1$) of said patient compared to $FEV_1$-value at the begin of the treatment.
58. The method according to item 33, wherein the event-free survival probability of the double lung transplanted patient being at risk to develop or being diagnosed with BOS is at least 60% after at least 48 weeks after the begin of the treatment, wherein the event is selected from a decline in $FEV_1$ of at least 20%, need for re-transplantation and/or death.
59. The method according to item 33, wherein the risk to experience an event selected from a decline in $FEV_1$ of at least 20%, need for re-transplantation and/or death within a period of at least 48 weeks from the beginning of the treatment for the double lung transplanted patient treated with the composition of the present invention in aerosolized form comprising CsA is reduced by at least 30% (abs.), preferably by at least 35% (abs.) compared to the risk to experience a corresponding event under treatment with standard immunosuppressive therapy (SOC) alone.
60. The method according to item 33, wherein the mean monthly change in $FEV_1$ ($\Delta FEV_1$/month) of the double lung transplanted patient being diagnosed with BOS remains substantially constant or has a value in the range of from about 0 to about 0.04 L/month.
61. The method according to item 33, wherein the absolute change in $FEV_1$ ($\Delta FEV_1$/abs.) between baseline (beginning of the treatment) and the end of the treatment period of the double lung transplanted patient being diagnosed with BOS is not more than 350 mL.
62. The method according to item 33, wherein the relative loss in $FEV_1$ ($\Delta FEV_1$/rel.) of the double lung transplanted patient being diagnosed with BOS relative to the loss of $FEV_1$ in a patient treated with standard immunosuppressive therapy (SOC) alone is at least 200 mL.
63. The method according to item 33, wherein the double lung transplanted patient being at risk to develop or being diagnosed with BOS has not been diagnosed with airway stenosis prior to the begin of the treatment, and preferably at week 24 after begin of the treatment, as ascertained by bronchoscopy with bronchoalveolar lavage (BAL).

64. The method according to item 33, wherein the double lung transplanted patient being at risk to develop or being diagnosed with BOS has not been diagnosed with an untreated infection prior to the begin of the treatment, and preferably at week 24 after the begin of the treatment.

65. The method according to item 33, wherein the maximum blood concentration of CsA in the double lung transplanted patient being at risk to develop or being diagnosed with BOS and being treated with the liquid composition comprising CsA is up to 100 ng/ml, preferably up to 60 ng/ml.

66. The method according to item 54 or 55, wherein the nebulizer can deliver a unit dose at a rate of at least about 0.1 mL/min.

65. The use of a composition comprising liposomal cyclosporine A (L-CsA) in the preparation of a medicament for the prevention of bronchiolitis obliterans syndrome (BOS) in a double lung transplanted patient, or for the treatment of BOS or for the prevention or delay of the progression of BOS in a double lung transplanted patient being diagnosed with BOS, wherein the composition is administered to said patient by inhalation of said composition in aerosolized form comprising a therapeutically effective dose of CsA.

DETAILED DESCRIPTION OF THE DRAWINGS

FIG. 1 shows a flow chart summarizing the details of the enrollment of single and double lung transplanted patients in the study described in the Example below. A total of 43 patients were assessed for eligibility, of which 23 patients met the eligibility criteria. One patient died and one patient withdrew from the study prior to randomization. 21 patients were randomized; 11 to the L-CsA treatment arm and 10 the SOC (Standard of care, i.e. standard immunosuppressive therapy) treatment arm. One patient in the L-CsA was withdrawn from the study due to progressive skin cancer during the 24-week follow-up. Traditional systemic immune suppression was discontinued because of progressive cancer in this patient and this patient was managed as intent to treat.

Figure 2:
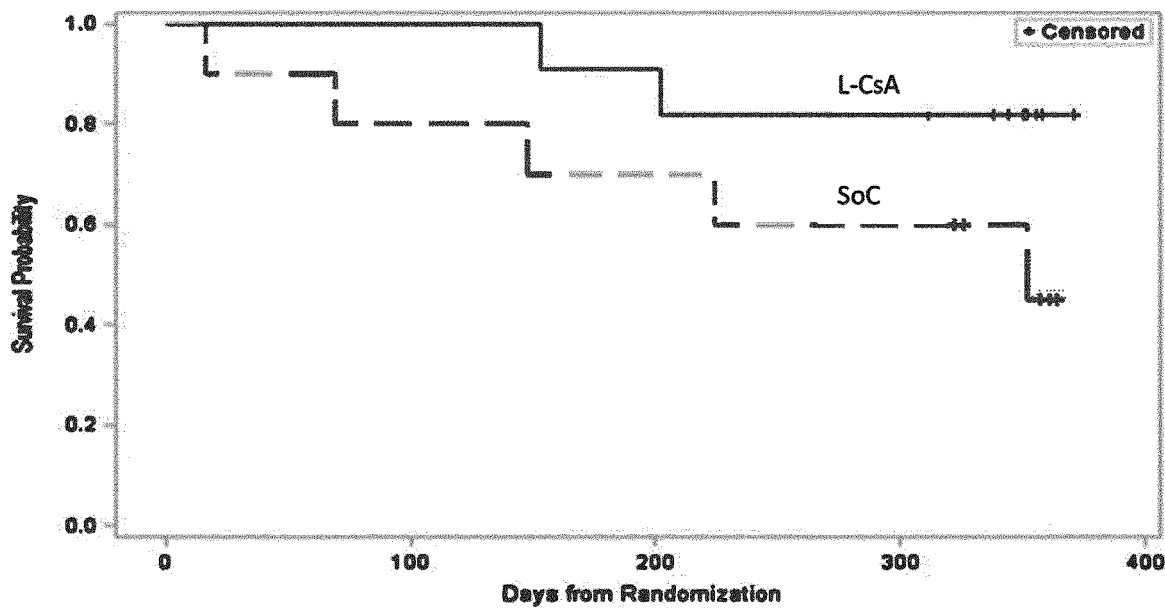
FIG. 2 shows a Kaplan-Meier plot of the BOS progression-free survival probability of single and double lung transplanted patients being diagnosed with BOS during the 48-week study period.

FIG. 2 shows a Kaplan-Meier plot of the BOS progression-free survival probability of single and double lung transplanted patients being diagnosed with BOS during the 48-week study period (i.e. without differentiation between single and double lung transplanted patients). Patients of the SOC group had a trend towards a higher risk of treatment failure during the study period (defined as: BOS progression, retransplant, or death) compared to L-CsA (Hazard Ratio (HR): 3.19; 95% Confidence Interval (95% CI): 0.62-16.50; p=0.14).

Figure 3:
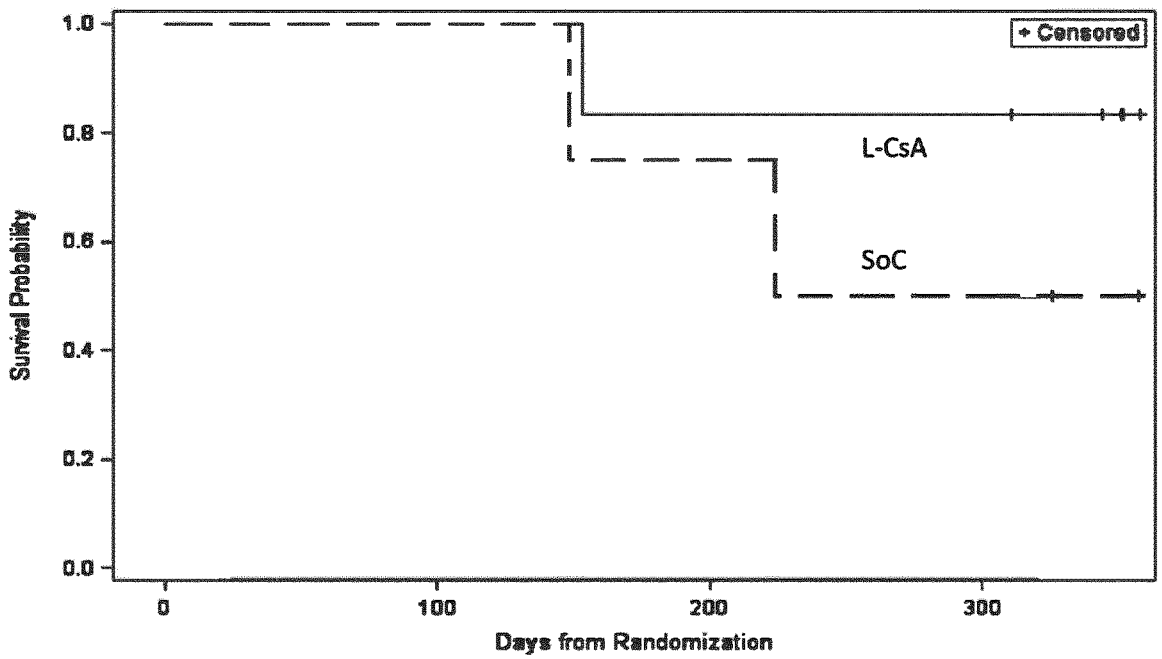
FIG. 3 shows a Kaplan-Meier plot of the event-free survival probability for double lung transplanted patients being diagnosed with BOS.

FIG. 3 shows a Kaplan-Meier plot of the event-free survival probability for double lung transplanted patients being diagnosed with BOS only (i.e. without the results for single lung transplanted patients). The event-free survival probability for double lung transplanted patients being diagnosed with BOS was 83% for the L-CsA treated group versus 50% for the group under SOC treatment alone. Furthermore, for the double lung transplanted patients the Hazard Ratio (HR) was 3.43 at a 95% CI of 0.31-37.95; p=0.29, meaning a 3.43-fold higher risk for experiencing BOS progression, need for a re-transplantation or death for the group of double lung transplanted patients under SOC treatment alone compared to the double lung transplanted patients under L-CsA treatment.

Figure 4:
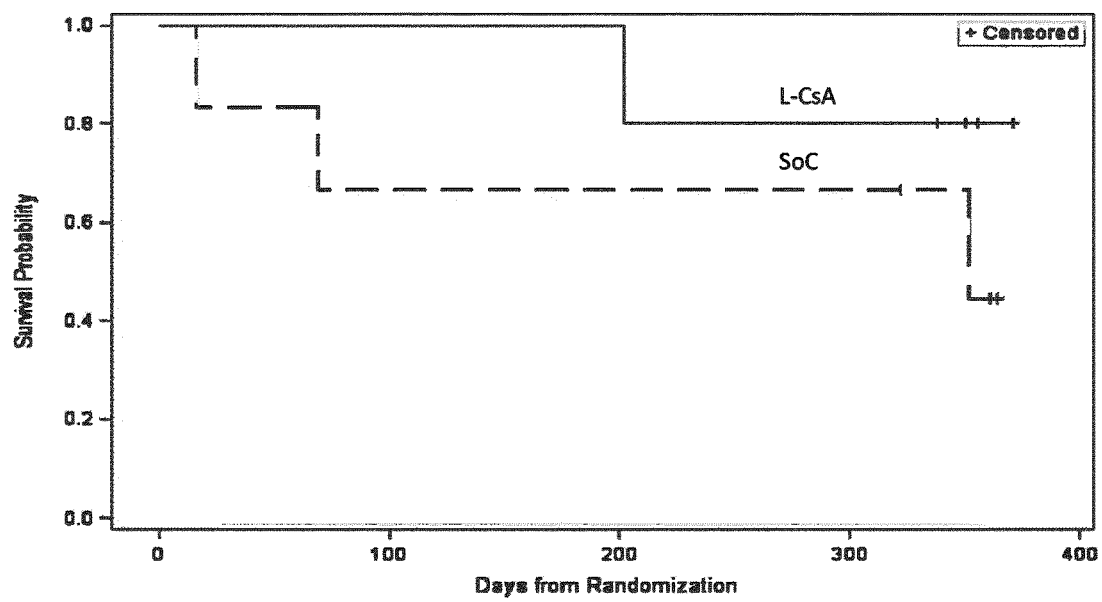
FIG. 4 shows a Kaplan-Meier plot of the event-free survival probability for single lung transplanted patients being diagnosed with BOS.

FIG. 4 shows a Kaplan-Meier plot of the event-free survival probability for single lung transplanted patients only (i.e. without the results for double lung transplanted patients): The event-free survival probability for single lung transplanted patients was 80% for the L-CsA treated group versus 50% for the group under SOC treatment alone. Furthermore, for the single lung transplanted patients the Hazard Ratio (HR) was 2.78 at a 95% CI of 0.29-26.98; p=0.36, meaning only a 2.78-fold higher risk for experiencing BOS progression, need for a re-transplantation or death for the group of single lung transplanted patients under SOC treatment alone compared to the single lung transplanted patients under L-CsA treatment.

Figure 5:
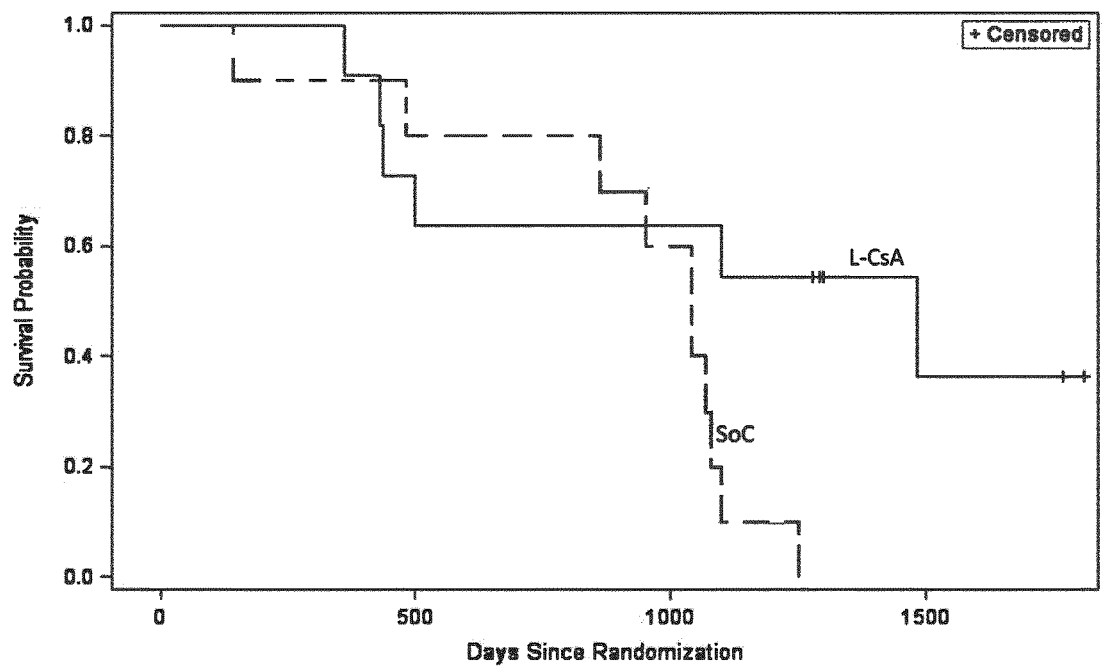
FIG. 5 shows a Kaplan-Meier plot of the overall survival probability of single and double lung transplanted patients being diagnosed with BOS at 5 years after randomization.

FIG. 5 shows the Kaplan-Meier plot of the overall survival probability of single and double lung transplanted patients at 5 years after randomization. The data demonstrates a marked improvement for L-CsA treated single or double lung transplanted patients: 5 patients out of 11 participants treated with L-CsA (45%) were alive at the 5 years follow-up compared to 0 of initially 10 patients treated with SOC alone. The median survival of the L-CsA treated patient group was 4.1 versus 2.9 years for the patient group treated with SOC alone (p=0.03). Cause of death was chronic allograft rejection with the exception of two cases, one dying from disseminated skin cancer (L-CsA) and renal failure (SOC).

Figure 6:
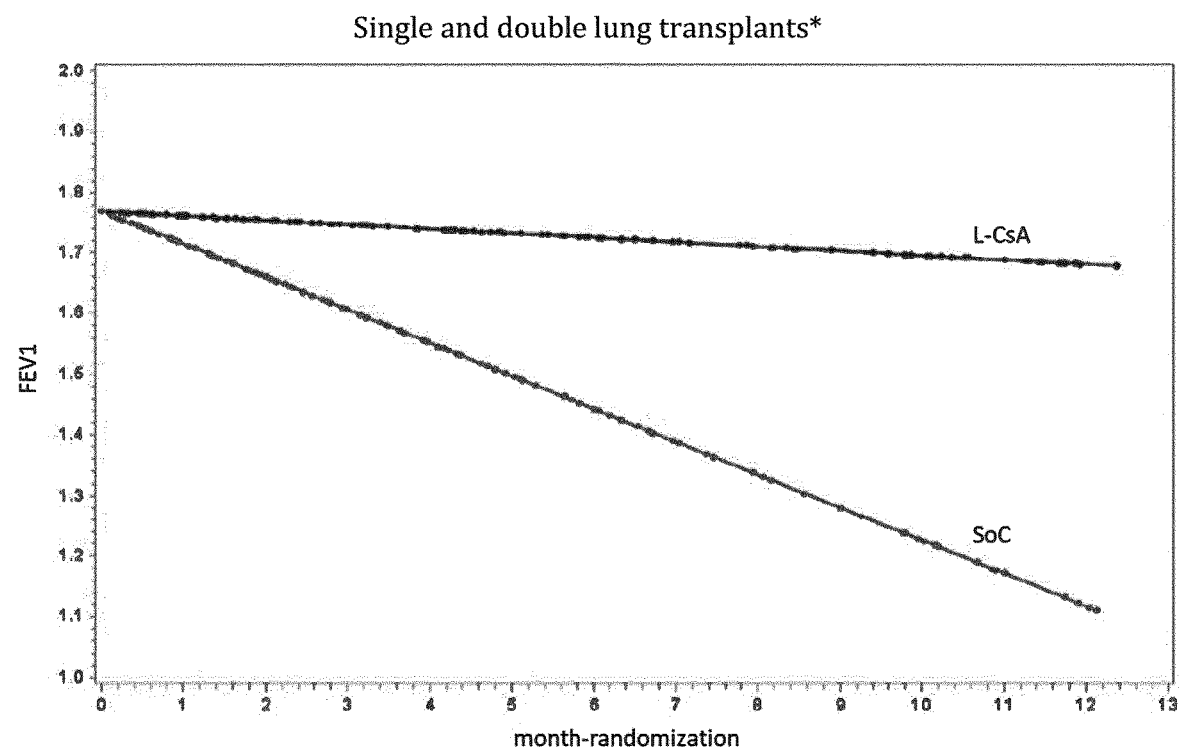
FIG. 6 shows a regression trend analysis of the course of the absolute $FEV_1$ values during the 48-weeks study period for single lung and double lung transplanted patients in the L-CsA treated arm (upper graph; "L-CsA") and for the SOC treated arm (lower graph; "SOC")

FIG. 6 shows an analysis of the overall $FEV_1$ development for single and double lung transplanted patients (i.e. without differentiation between single and double lung transplanted patients) after adjustment of the measured data for pre-randomization and post randomization in a random slope mixed model: In the L-CsA treated patient arm (11 patients) a slight decrease of the mean absolute $FEV_1$ values was observed starting from approx. 1.75 L at the time of randomization to 1.70 L at the end of the 48-week period, whereby for the SOC treated patient group (10 patients; one patient had no post-randomization PFT measurements due to need for mechanical ventilation; this patient was included into the $FEV_1$ slope calculations: An $FEV_1$-value of 0 was imputed at the time the patient went on mechanical ventilation; this patient had no post-randomization PFT (pulmonary function testing) measurements) a steady and significant decrease in $FEV_1$-values from approx. 1.75 L to approx. 1.15 L was observed. In this overall analysis of single and double lung transplanted patients the monthly change in $FEV_1$ ($\Delta FEV_1$/month) was −0.007 at a 95% CI of −0.033 to 0.018 for the L-CsA-treated patient group versus −0.054 at a 95% CI of −0.100 to −0.006 (p=0.10).

Figure 7:
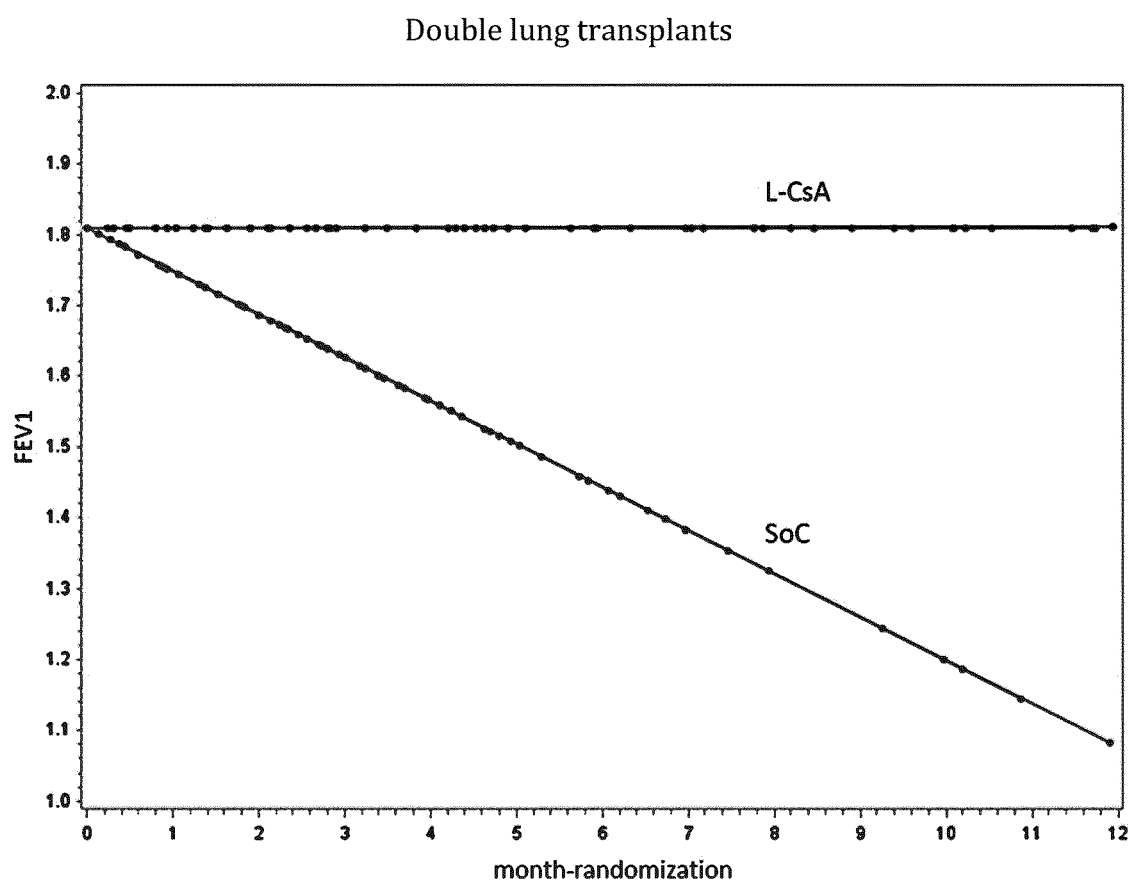
FIG. 7 shows a regression trend analysis of the course of the absolute $FEV_1$ values during the 48-weeks study period for double lung transplanted patients in the L-CsA treated arm (upper graph; "L-CsA") and for the SOC treated arm (lower graph; "SOC")

FIG. 7 shows the development of the mean absolute $FEV_1$ values during the 48-weeks study period for double lung transplanted patients (i.e. without the results for single lung transplanted patients) in the L-CsA treated arm (upper graph; "L-CsA") and for the SOC treated arm (lower graph; "SOC"): In the L-CsA treated patient arm (6 patients), the mean absolute $FEV_1$ values stayed approx. constant at 1.8 L throughout the 48-week period. In contrast to this, for the double lung transplanted patent group in the SOC arm (4 patients) the mean absolute $FEV_1$-values decreased markedly from approx. 1.8 L to approx. 1.1 L over the same period. Accordingly, the monthly change in $FEV_1$ ($\Delta FEV_1$/month) for double lung transplanted patients was 0.000 at a 95% CI of −0.049 to 0.049 for the L-CsA-treated arm and −0.061 at a 95% Cl of −0.096 to 0.026 (p=0.07) for the SOC treated arm.

Figure 8:
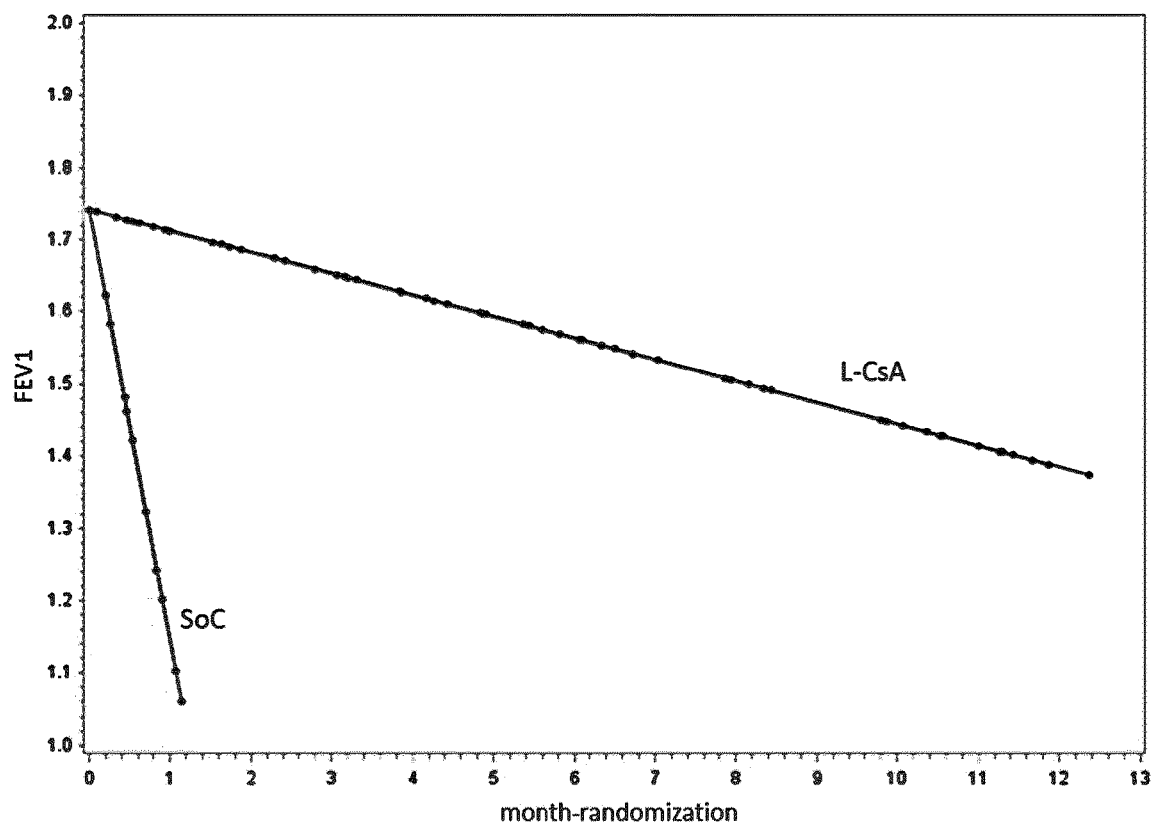
FIG. 8 shows a regression trend analysis of the course of the absolute $FEV_1$ values during the 48-weeks study period for single lung transplanted patients in the L-CsA treated arm (upper graph; "L-CsA") and for the SOC treated arm (lower graph; "SOC").

FIG. 8 shows the development of the mean absolute $FEV_1$ values during the 48-weeks study period for single lung transplanted patients (i.e. without the results for double lung transplanted patients) in the L-CsA treated arm (upper graph; "L-CsA") and for the SOC treated arm (lower graph;

"SOC"): In the L-CsA treated patient arm (5 patients) a decrease of the mean absolute FEV$_1$ values from approx. 1.75 L immediately after randomization to approx. 1.4 L at week 48 after randomization was observed. For the single lung transplanted patent group in the SOC arm (6 patients; one patient had no post-randomization PFT measurements due to need for mechanical ventilation; patient was included into FEV$_1$ slope calculations: An FEV$_1$-value of 0 was imputed at the time the patient went on mechanical ventilation; this patient had no post-randomization PFT (pulmonary function testing) measurements) the mean FEV$_1$-values decreased markedly from approx. 1.75 L to approx. 1.05 L over the same period (due to the calculation method the graph for the SOC treated arm ends at month 1). Accordingly, the monthly change in FEV$_1$ ($\Delta$FEV$_1$/month) for double lung transplanted patients was −0.029 at a 95% CI of −0.019 to 0.001 for the L-CsA-treated arm and −0.600 at a 95% Cl of −2.074 to 0.872 (p=0.37) for the SOC treated arm.

The following Examples serves to illustrate the invention; however, it is not to be understood as restricting the scope of the invention:

EXAMPLES

Example 1: In Vitro Aerosol Characterization of Liquid CsA Formulation

A liposomal cyclosporine liquid formulation for inhalation consisting of the active substance CsA (Ph.Eur.) and the excipients lipoid S100, polysorbate 80, disodium edetate, disodium hydrogen phosphate dodecahydrate and sodium dihydrogen phosphate monohydrate was prepared. The formulation was adjusted to physiologically tolerable values of pH (6.5±0.2) and osmolality (350-450 mOsmol/kg).

An aerosol was generated using an eFlow® nebulizer using a mixing chamber with a volume of about 95 ml. The aerosol generated with this nebulizer was characterized using breath simulation, laser diffraction and impactor measurements. The results of these measurements are summarized in Table 1.

TABLE 1

Aerosol characteristics of a liposomal cyclosporine (L-CsA) formulation nebulized with an eFlow ® nebulizer

| | |
|---|---|
| Nominal drug amount [mg] | 15.0 ± 0.4 |
| MMD [μm] | 2.8 ± 0.1 |
| DD [%] | 75.9 ± 2.6 |
| RD [% <5 μm] | 67.7 ± 2.8 |
| RD [%, <3.3 μm] | 46.7 ± 2.9 |

Values expressed as mean ± standard deviation;
MMD = mass median diameter;
DD = delivered dose (ex-mouthpiece);
RD = respirable dose A delivered dose (DD) (amount ex-mouthpiece) of 76% and a respirable dose (RD) of droplets smaller than 3.3 μm of approximately 47% were achieved. Particles smaller than 3.3 pm have a high probability to deposit in the distal part of the lung which is regarded as the optimal drug deposition site for an efficacious lung graft protection. In general, aerosol droplets smaller than 5 μm have a high probability to deposit in the whole lung and should be considered for lung transplant protection to some extent as well. The respirable dose of droplets smaller than 5 μm was approximately 68%.

On the basis of these results, it can be concluded that for a nominal drug amount of 10 mg, the corresponding delivered dose (in mg) will be approximately 7.6 mg CsA. The respirable dose (in mg) for droplets below 5 and 3.3 pm will be approximately 6.8 and 4.7 mg CsA, respectively.

Example 2: In Vitro Aerosol Characterization of Reconstituted CsA Formulation Sucrose was added as a lyoprotectant to the formulation described in Example 1. Afterwards, the formulation was lyophilized. Immediately before nebulization, the formulation was reconstituted with 2.3 ml 0.25% saline. The liposome size was in the range of 40-100 nm (0.040-0.10 μm) with a polydispersity index of less than 0.40 after reconstitution.

The reconstituted formulation was nebulized with an eFlow® nebulizer which had the same inhalation chamber as the nebulizer in Example 1, i.e. a mixing chamber with a volume of about 95 ml. The results of the aerosol characterization data generated with the reconstituted formulation are shown in Table 2.

The results showed no substantial differences in comparison with the results obtained in Example 1.

TABLE 2

Aerosol characteristics of a reconstituted liposomal cyclosporine formulation nebulized with an eFlow ® nebulizer

| | |
|---|---|
| Fill volume [ml] | 2.5 |
| Nominal drug amount [mg] | 10.4 ± 0.0 |
| MMAD [μm] | 3.3 ± 0.1 |
| GSD | 1.5 ± 0.0 |
| DD [%] | 75.3 ± 2.6 |
| DD [mg] | 7.9 ± 0.3 |
| RD [%, <5 μm] | 65.3 ± 2.8 |
| RD [mg, <5 μm] | 6.8 ± 0.3 |
| RD [%, <3.3 μm] | 37.7 ± 2.2 |
| RD [mg, <3.3 μm] | 3.9 ± 0.2 |
| Nebulization time [min] | 7.4 ± 0.1 |

Values expressed as mean ± standard deviation;
MMAD = mass median aerodynamic diameter;
GSD = geometric standard deviation;
DD = delivered dose (ex-mouth-piece);
RD = respirable dose

Example 3: Clinical Trial with Inhaled Cyclosporine in the Treatment of BOS

Study Enrollment:

43 patients were assessed for eligibility, of which 23 met eligibility criteria. One patient died and one patient withdrew prior to randomization. 21 patients were randomized; 11 patients to the L-CsA treatment arm and 10 patients the SOC treatment arm. (FIG. 1) One patient in L-CsA was withdrawn from the study due to progressive skin cancer during the 24-week follow-up phase. In this case, standard systemic immune suppression was discontinued.

BOS 1 or BOS 2 patients were eligible if free from untreated infection and airway stenosis by bronchoscopy with bronchoalveolar lavage (BAL) performed before randomization and at week 24 and when clinically indicated.

Bronchiolitis obliterans syndrome (BOS) grading was applied as follows: Based on bi-monthly FEV$_1$ measurements, a BOS evaluation was performed on a continuous basis. The definition of BO is according to modified BOS criteria from the publication of Estenne et al. (Estenne M, et al. Bronchiolitis obliterans syndrome 2001: an update of the diagnostic criteria. *J Haert Lung Transplant*. 2002; 21 (3): 297-310). The following definitions and criteria were applied:

BOS 0: $FEV_1$ >90% of baseline
BOS 0-p: $FEV_1$ 81% to 90% of baseline
BOS 1: $FEV_1$ 66% to 80% of baseline
BOS 2: $FEV_1$ 51% to 65% of baseline
BOS 3: $FEV_1$ 50% or less of baseline Study Design:

21 single or double lung transplanted patients diagnosed with BOS grade 1 or 2 were enrolled into this single-center, randomized, open label clinical trial evaluating the addition of aerosolized L-CsA plus standard immunosuppression for BOS 1 and BOS 2 (grades 1-2) compared to standard immunosuppression alone (SOC).

Patients were scheduled to be followed for 48 weeks (24 weeks with administration of L-CsA as described below and 24 weeks follow-up without administration in the study arm). Patients in in the SOC arm could cross over to the group under L-CsA medication after meeting the primary end-point or in the L-CsA arm if the primary end-point occurred during the 24 weeks follow-up.

Patients were allocated to receive twice daily either 5 mg/1.25 ml or 10 mg/2.5 ml L-CsA therapy, for single lung transplant (SLT) or double lung transplant (DLT) patients (L-CsA arm), respectively, in addition to Standard of Care systemic immunosuppression or Standard of Care systemic immunosuppression alone (SOC arm) for 24 weeks, followed by a 24-weeks without administration of the study drug (L-CsA).

The L-CsA formulations were used in form of a reconstituted lyophilizate in 0.25% saline and were nebulized using an eFlow® nebulizer (PARI, Germany). A filter was placed at the exhaust valve of the inhalation chamber. Furthermore, the nebulizer was designed in such way that it could only be operated when a key card (eFlow® chip card) on which inhalation time and duration were monitored was introduced into the nebulizer.

Treatment Protocol:

Patients were randomly allocated to either the L-CsA arm (treatment) or the SOC arm (no treatment with CsA). L-CsA was administered at 5 mg or 10 mg twice daily (for single lung or double lung transplant patients, respectively), in addition to standard immunosuppression consisting of tacrolimus (0.06 mg/kg; trough levels 8-12 ng/ml), mycophenolate mofetil (1 gm PO bid) or sirolimus (2 mg PO day; level 7-12 ng/ml) and prednisone (20 mg/day), while the SOC group received standard immunosuppression alone. When utilized, combined sirolimus and tacrolimus blood levels were maintained between 4-5 ng/ml. Adjustments were made by the treating clinicians' based assessment of clinical parameters and protocols at the study center. Infection prophylaxis included valcyte, voriconazole, and sulfamethoxazole/trimethoprim. Enhanced immune suppression consisted of pulsed corticosteroids (intravenous methylprednisolone at a dose of 1 gm per day for 3 days or oral prednisone (100 mg tapered to 10 mg over 14 days) or antithymocyte globulin (1.5 mg per kilogram per day for 3 to 5 days). Progression of BOS by $FEV_1$ was validated before and after treatment for concurrent illnesses measured at least three weeks apart and verified by two co-investigators.

End Points:

The primary endpoints of BOS progression were:
1) ≥20 percent decline in $FEV_1$ from randomization;
2) death or
3) re-transplantation.

Secondary end-points included lung function changes, aerosol tolerability, pharmacokinetics, cytokine changes and drug toxicity. Routine laboratory data was collected at 30-day intervals. Cytokines (IL-1β, IL-2, IL-6, IL-8, IL-10, IL-17, IFN-γ and TNF-α) were measured prior to randomization and at the end-of-treatment period from BAL fluid by multiplex assays (BioRad®) using a Luminex 100 reader and analyzed using BioRad's Software.

Statistical Analysis:

The combined primary end-point of BOS progression and overall patient survival was compared by the method of Kaplan and Meier and log-rank testing. Transplant type as a factor affecting survival was assessed by Cox proportional hazards model. Data are presented with hazard ratios (HR) and 95% confidence intervals (95% CI). For lung function analyses, multivariate linear mixed-effects statistical models (PROC MIXED, SAS version 9.1.3; SAS Institute, Cary, NC) were utilized (Laird N M, Ware J H. Random-effects models for longitudinal data; Biometric 1982; 38:963-974). The mixed model analyzed intragroup and intergroup values pre-randomization and post-randomization adjusting for changes that could potentially influence post-randomization function. Cytokine values were compared by a 2-way ANOVA. A mixed model statistic was used to analyze laboratory values and drug levels. All results including cross over cases were analyzed as intention to treat. A total of 242 pulmonary function tests, 42 bronchoalveolar lavage (BAL) specimens for cytokines and 603 blood samples were analyzed.

Results

Patient Characteristics:

11 patients were randomized to the L-CsA arm and 10 to the SOC arm (see FIG. 1). Baseline characteristics and clinical management in the two groups were similar. The distribution of baseline demographic characteristics did not differ appreciably between groups. The mean treatment duration with L-CsA was 167.5±12.5 days. No adverse event required study withdrawal due to L-CsA and no patient was lost to follow-up.

Two cases who met the primary end-point in the SOC group received crossover therapy with L-CsA and one patient randomized to L-CsA reinitiated L-CsA ($FEV_1$ decline >20%) following the initial 24-week drug administration interval. One patient was withdrawn from the study after the initial 24 weeks L-CsA interval as cessation of systemic immunosuppression was required due to recurrent skin cancers.

Stabilization of Bronchiolitis Obliterans:

Event-free survival probability was analyzed by means of Kaplan-Meier survival analysis overall, i.e. without stratification by single and double lung transplanted patients as well as with stratification by single or double lung transplantation (herein also referred to as "SLT" or "DLT", respectively). Patients terminating their participation in the trial at any time and for any reason without experiencing an endpoint event were censored.

To perform the analyses, a Full Analysis Set (FAS) and a Per-Protocol Analysis Set (PPS) were defined. The FAS included all patients who received at least one dose of the investigational treatment. The PPS included all patients from the FAS without any major protocol violations that were considered to imperil the scientific aspects and interpretation of the study results (e.g. wrong inclusions, adherence of less than 75%, prohibited concomitant medications).

A stabilization of BOS was observed according to the primary study end-point for the L-CsA treated group compared to the SOC group and in double and single lung recipients analyzed distinctly: In 9 of the 11 patients treated with L-CsA and SOC the event-free survival probability was 82% versus 50% for 5 out of 10 patients treated with SOC alone. (HR (Hazard Ratio): 3.19; 95% CI (Confidence Interval): 0.62-16.50; p=0.14; see FIG. 2)

For double lung transplanted patients, the event-free survival probability was 83% for the L-CsA treated group versus 50% for the group under SOC treatment alone. Furthermore, for the double lung transplanted patients the Hazard Ratio (HR) was 3.43 at a 95% CI of 0.31-37.95; p=0.29, meaning a 3.43-fold higher risk for experiencing BOS progression, need for a re-transplantation or death for the group of double lung transplanted patients und or SOC treatment alone compared to the double lung transplanted patients under L-CsA treatment. (see FIG. 3)

For single lung transplanted patients, the event-free survival probability was 80% for the L-CsA treated group versus 50% for the group under SOC treatment alone. Furthermore, for the single lung transplanted patients the Hazard Ratio (HR) was 2.78 at a 95% CI of 0.29-26.98; p=0.36, meaning only a 2.78-fold higher risk for experiencing BOS progression, need for a re-transplantation or death for the group of single lung transplanted patients under SOC treatment alone compared to the single lung transplanted patients under L-CsA treatment. (see FIG. 4)

Of the two cases who experienced a primary event in the L-CsA group, one responded to L-CsA re-initiation (based on primary end point criteria) and the other was re-transplanted; of the 5 primary events in the SOC group, 2 were retransplanted, 2 required mechanical ventilation and 1 of two cases who crossed over from SOC responded to L-CsA.

As can be seen from Kaplan-Meier of FIGS. 2 to 4, the effect of the L-CsA administered to the double lung transplanted patients is significantly higher than for the single transplanted patients when analyzed over the full 48 weeks treatment- and observation period. The hazard ratio (HR) as a measure for survival probability of 1:2.78 (L-Cs-A:SOC) for single lung transplanted patients is significantly less favorable than for double lung transplanted patents with a ratio of 1:3.43 (L-CsA:SOC).

The overall survival probability at 5 years after randomization demonstrated a marked improvement for L-CsA treated single or double lung transplanted patients: 5 patients out of 11 participants treated with L-CsA (45%) were alive at the 5 years follow-up compared to 0 of initially 10 patients treated with SOC alone. The median survival of the L-CsA treated patient group was 4.1 versus 2.9 years for the patient group treated with SOC alone (p=0.03; see FIG. 5). Cause of death was chronic allograft rejection with the exception of two cases, one dying from disseminated skin cancer (L-CsA) and renal failure (SOC).

Lung Function Changes

As a measure for the stabilization or progression of BOS in single and double lung transplanted patients being diagnosed with BOS in the L-CsA arm and the SOC-arm the changes in the $FEV_1$ values (Forced Exhaled Volume after the first second of forced expiration) have been observed during the 48-week study period.

As shown in FIG. 6 the analysis of the overall $FEV_1$ development for single and double lung transplanted patients after adjustment of the measured data for pre-randomization and post randomization in a random slope mixed model gives a clear result: In the L-CsA treated patient arm (11 patients) a slight decrease of the mean absolute $FEV_1$ values was observed starting from approx. 1.75 L at the time of randomization to 1.70 L at the end of the 48-week period, whereby for the SOC treated patient group (10 patients; one patient had no post-randomization PFT measurements due to need for mechanical ventilation; this patient was included into the $FEV_1$ slope calculations:

An $FEV_1$-value of 0 was imputed at the time the patient went on mechanical ventilation; this patient had no post-randomization PFT (pulmonary function testing) measurements) a steady and significant decrease in $FEV_1$-values from approx. 1.75 L to approx. 1.15 L was observed. It should be noted that in this overall analysis of single and double lung transplanted patients the monthly change in $FEV_1$ ($\Delta FEV_1$/month) was −0.007 at a 95% CI of −0.033 to 0.018 for the L-CsA-treated patient group versus −0.054 at a 95% CI of −0.100 to −0.006 (p=0.10).

As shown in FIG. 7 the development of the absolute $FEV_1$ values during the 48-weeks study period for double lung transplanted patients alone in the L-CsA treated arm (upper graph; "L-CsA") and for the SOC treated arm (lower graph; "SOC") gives an even more significant result: In the L-CsA treated patient arm (6 patients), the mean absolute $FEV_1$ values stayed approx. constant at 1.8 L throughout the 48-week period. In contrast to this, for the double lung transplanted patent group in the SOC arm (4 patients) the mean absolute $FEV_1$-values decreased markedly from approx. 1.8 L to approx. 1.1 L over the same period. Accordingly, it should be noted that the monthly change in $FEV_1$ ($\Delta FEV_1$/month) for double lung transplanted patients was 0.000 at a 95% CI of −0.049 to 0.049 for the L-CsA-treated arm and −0.061 at a 95% Cl of −0.096 to −0.026 (p=0.07) for the SOC treated arm.

As shown in FIG. 8 the development of the absolute $FEV_1$ values during the 48-weeks study period for single lung transplanted patients alone in the L-CsA treated arm (upper graph; "L-CsA") and for the SOC treated arm (lower graph; "SOC") shows a similar trend: In the L-CsA treated patient arm (5 patients) a decrease of the mean absolute $FEV_1$ values from approx. 1.75 L immediately after randomization to approx. 1.4 L at week 48 after randomization was observed. For the single lung transplanted patent group in the SOC arm (6 patients; one patient had no post-randomization PFT measurements due to need for mechanical ventilation; patient was included into $FEV_1$ slope calculations: An $FEV_1$-value of 0 was imputed at the time the patient went on mechanical ventilation; this patient had no post-randomization PFT (pulmonary function testing) measurements) the mean $FEV_1$-values decreased markedly from approx. 1.75 L to approx. 1.05 L over the same period (due to the calculation method the graph for the SOC treated arm ends at month 1). Accordingly, the monthly change in $FEV_1$ ($\Delta FEV_1$/month) for double lung transplanted patients was −0.029 at a 95% CI of −0.019 to 0.001 for the L-CsA-treated arm and −0.600 at a 95% Cl of −2.074 to 0.872 (p=0.37) for the SOC treated arm.

The invention claimed is:

1. A method for treating bronchiolitis obliterans syndrome (BOS) in a double lung transplanted patient, or for delaying the onset or progression of BOS in a double lung transplanted patient being diagnosed with BOS, the method comprising administering to said patient by inhalation a composition comprising liposomal cyclosporine A (L-CsA) in aerosolized form comprising a therapeutically effective dose of cyclosporine A.

2. The method according to claim 1, wherein the double lung transplanted patient is diagnosed with BOS 1 or BOS 2.

3. The method according to claim 1, wherein the composition is a liquid composition comprising an aqueous liquid vehicle.

4. The method according to claim 3, wherein the aqueous liquid vehicle essentially consists of saline.

5. The method according to claim 4, wherein the saline has a concentration of 0.25%.

6. The method according to claim 3, wherein the liquid composition has a CsA concentration in the range of from 0.5 to 10 mg/mL.

7. The method according to claim 3, wherein the liquid composition is prepared by reconstitution of liposomal cyclosporine A in lyophilized form.

8. The method according to claim 1, wherein cyclosporine A is administered at an effective daily dose in the range of 5 to 30 mg.

9. The method according to claim 1, wherein cyclosporine A is administered at an effective daily dose of 20 mg.

10. The method according to claim 1, wherein the composition is administered to said patient twice daily.

11. The method according to claim 1, wherein the composition is administered over a period of at least 24 weeks.

12. The method according to claim 1, wherein the double lung transplanted patient is co-treated with standard immunosuppressive therapy.

13. The method according to claim 1, wherein the composition is aerosolized with an electronic vibrating membrane nebulizer.

14. The method according to claim 1, wherein the composition is inhaled with an adherence of at least 75%.

15. The method according to claim 1, wherein the onset or progression of BOS of the double lung transplanted patient being diagnosed with BOS is reduced to a level of up to 20% decline of the forced expiratory volume in one second ($FEV_1$) of said patient compared to $FEV_1$-value at the beginning of the treatment.

16. The method according to claim 1, wherein an event-free survival probability of the double lung transplanted patient being diagnosed with BOS is at least 60% after at least 48 weeks from the beginning of the treatment, wherein an event is selected from a decline in $FEV_1$ of at least 20%, need for re-transplantation, and/or death.

17. The method according to claim 1, wherein a mean monthly change in $FEV_1$ ($\Delta FEV_1$/month) of the double lung transplanted patient being diagnosed with BOS remains substantially constant or has a value in the range of from about 0 to about 0.04 L/month.

18. The method according to claim 1, wherein a risk to experience an event selected from a decline in $FEV_1$ of at least 20%, need for re-transplantation, and/or death within a period of at least 48 weeks from the beginning of the treatment for the double lung transplanted patient treated with the composition in aerosolized form comprising CsA is reduced by at least 30% (abs.) compared to the risk to experience a corresponding event under treatment with standard immunosuppressive therapy (SOC) alone.

19. The method according to claim 18, wherein the risk is reduced by at least 35% (abs.).

20. The method according to claim 1, wherein an absolute change in $FEV_1$ ($\Delta FEV_1$/abs.) between baseline (beginning of the treatment) and an end of a treatment period of the double lung transplanted patient being diagnosed with BOS is not more than 350 mL.

21. The method according to claim 1, wherein a relative loss in $FEV_1$ ($\Delta FEV_1$/rel.) of the double lung transplanted patient being diagnosed with BOS relative to a loss of $FEV_1$ in a patient treated with standard immunosuppressive therapy (SOC) alone is at least 200 mL.

22. The method according to claim 1, wherein the double lung transplanted patient has not been diagnosed with airway stenosis prior to the beginning of the treatment as ascertained by bronchoscopy with bronchoalveolar lavage (BAL).

23. The method according to claim 22, wherein the double lung transplanted patient has not been diagnosed with airway stenosis prior to week 24 after beginning of the treatment.

24. The method according to claim 1, wherein the double lung transplanted patient being diagnosed with BOS has not been diagnosed with an untreated infection prior to randomization.

25. The method according to claim 24, wherein the double lung transplanted patient being diagnosed with BOS has not been diagnosed with an untreated infection prior to week 24 after the beginning of the treatment.

26. The method according to claim 1, wherein a maximum blood concentration of CsA in the double lung transplanted patient being diagnosed with BOS and being treated with the liquid composition comprising CsA is up to 100 ng/ml.

27. The method according to claim 26, wherein the maximum blood concentration of CsA is up to 60 ng/mL.

* * * * *